United States Patent
Morimoto et al.

(10) Patent No.: US 10,501,480 B2
(45) Date of Patent: Dec. 10, 2019

(54) OPTICAL FILM

(71) Applicant: Sumitomo Chemical Company, Limited, Tokyo (JP)

(72) Inventors: Masao Morimoto, Osaka (JP); Noriyuki Hida, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/494,764

(22) Filed: Apr. 24, 2017

(65) Prior Publication Data

US 2017/0305930 A1  Oct. 26, 2017

(30) Foreign Application Priority Data

Apr. 26, 2016  (JP) .................. 2016-088396

(51) Int. Cl.
| | | |
|---|---|---|
| *G02F 1/1333* | (2006.01) |
| *C07D 513/04* | (2006.01) |
| *C08F 222/20* | (2006.01) |
| *C09B 31/14* | (2006.01) |
| *C09B 33/16* | (2006.01) |
| *C09B 35/34* | (2006.01) |
| *C09K 19/38* | (2006.01) |
| *C09K 19/60* | (2006.01) |
| *G02B 1/08* | (2006.01) |
| *G02B 5/30* | (2006.01) |
| *C09K 19/30* | (2006.01) |
| *C09B 31/043* | (2006.01) |
| *C08F 222/10* | (2006.01) |
| *C09K 19/04* | (2006.01) |

(52) U.S. Cl.
CPC ...... *C07D 513/04* (2013.01); *C08F 222/1006* (2013.01); *C08F 222/20* (2013.01); *C09B 31/043* (2013.01); *C09B 31/14* (2013.01); *C09B 33/16* (2013.01); *C09B 35/34* (2013.01); *C09K 19/3068* (2013.01); *C09K 19/3809* (2013.01); *C09K 19/3852* (2013.01); *C09K 19/601* (2013.01); *G02B 1/08* (2013.01); *G02B 5/3016* (2013.01); *C08F 2800/20* (2013.01); *C09K 2019/0448* (2013.01)

(58) Field of Classification Search
CPC ............ C09K 19/3068; C09K 19/3809; C09K 19/3852; C09K 19/601; C09K 2019/0448; G02F 1/1333; C09B 31/043; C09B 31/14; C09B 33/16; C09B 35/34; C07D 513/04; G02B 1/08; G02B 5/3016; C08F 222/20; C08F 222/1006; C08F 2800/20
USPC .................................................... 252/299.61
See application file for complete search history.

(56) References Cited

U.S. PATENT DOCUMENTS 7,763,330 B2    7/2010  Lub et al.
2017/0306237 A1*  10/2017  Morimoto ............... C09B 39/00

FOREIGN PATENT DOCUMENTS

| JP | 2007-510946 A | 4/2007 | |
| JP | 2013101328 A | 5/2013 | |
| JP | 2013-227532 | * 11/2013 | ............. C09K 19/60 |

* cited by examiner

*Primary Examiner* — Geraldina Visconti
(74) *Attorney, Agent, or Firm* — Panitch Schwarze Belisario & Nadel LLP

(57) ABSTRACT

Provided is an optical film which has a maximum absorption at a wavelength in the range of 600 to 680 nm, has a high dichroic ratio, and is excellent in light resistance. The optical film includes: a polymer of a polymerizable liquid crystal compound; and a compound represented by the following general formula (1).

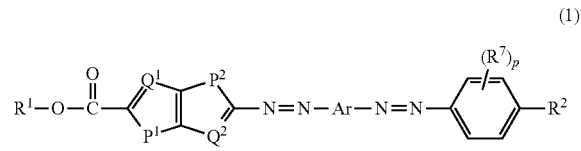

13 Claims, No Drawings

OPTICAL FILM

BACKGROUND OF THE INVENTION

Field of the Invention

The present invention relates to an optical film.

Description of the Related Art

JP-T-2007-510946 (published in 26 Apr. 2007) and JP-A-2013-101328 (published in 23 May 2013) each describe a polarizing film containing a dichroic light-absorbing compound (dichroic dye) dispersed in an oriented polymerizable liquid crystal compound.

However, the polarizing film described in each of JP-T-2007-510.946 (published in 26 Apr. 2007) and JP-A-2013-101328 (published in 23 May 2013) has an insufficient dichroic ratio and insufficient light resistance, and therefore in the field of polarizing films (optical films) containing a dichroic dye as described above, an optical film superior in light resistance to conventional optical films is desired.

SUMMARY OF THE INVENTION

For solving the above-described problem, the present invention includes the followings.
<1> An optical film including: a polymer of a polymerizable liquid crystal compound; and a compound represented by the following general formula (1):

[Chemical Formula 1]

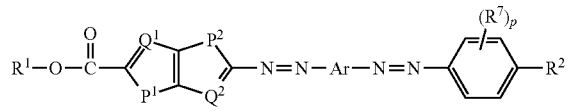
(1)

[in the general formula (1), $R^1$ represents an alkyl group having 1 to 11 carbon atoms;
$P^1$ and $P^2$ each independently represent —S—, —O— or —N($R^{12}$)—, $R^{12}$ represents a hydrogen atom or an alkyl group having 1 to 4 carbon atoms, and $Q^1$ and $Q^2$ each independently represent =N— or =CH—; Ar represents a group represented by the following general formula (Ar-1) or (Ar-2):

[Chemical Formula 2]

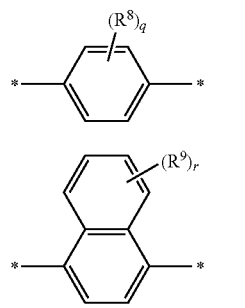

(in the above general formula, * represents a binding part with N);
$R^2$ represents a group selected from the following groups:

[Chemical Formula 3]

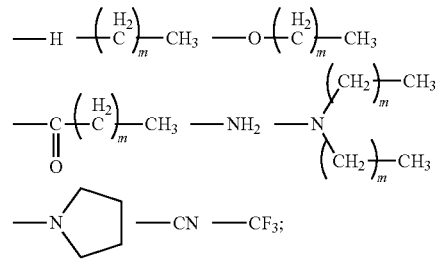

$R^7$ to $R^9$ are substituents other than a hydrogen atom, and each independently represent an alkyl group having 1 to 4 carbon atoms, an alkoxy group having 1 to 4 carbon atoms, a halogen atom or a cyano group, and one or more of hydrogen atoms in the alkyl group or the alkoxy group may be substituted with a halogen atom or a hydroxy group;
m represents an integer of 0 to 10, and when one group has two occurrences of m, the two occurrences of m may be mutually the same or different; and p, q and r each independently represent an integer of 0 to 2].
<2> The optical film according to <1>, wherein the compound represented by the general formula (1) is a compound represented by the following general formula (2):

[Chemical Formula 4]

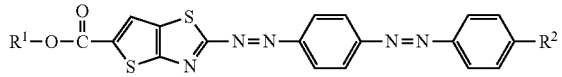
(2)

[in the general formula (2), $R^1$ and R have the same meaning as $R^1$ and $R^2$ in the general formula (1)].
<3> The optical film according to <1> or <2>, including two or more compounds which have mutually different structures and which are represented by the general formula (1).
<4> The optical film according to <3>, wherein the two or more compounds which have mutually different structures and which are represented by the general formula (1) have mutually different structures only in $R^1$ in the general formula (1).
<5> The optical film according to any one of <1> to <4>, wherein the polymerizable liquid crystal compound is a compound which shows a smectic liquid crystal phase.
<6> The optical film according to any one of <1> to <5>, wherein the polymerizable liquid crystal compound is a compound represented by the following general formula (4):

$$U^1—V^1—W^1—X^1—Y^1—X^2—Y^2—X^3—W^2—V^2—U^2 \quad (4)$$

(in the formula, $X^1$, $X^2$ and $X^3$ each independently represent a 1,4-phenylene group optionally having a substituent, or a cyclohexane-1,4-diyl group optionally having a substituent, with the proviso that at least one of $X^1$, $X^2$ and $X^3$ is a 1,4-phenylene group optionally having a substituent, and —$CH_2$— in the cyclohexane-1,4-diyl group may be substituted with —O—, —S— or —NR—, where R represents an alkyl group having 1 to 6 carbon atoms, or a phenyl group;
$Y^1$ and $Y^2$ each independently represent a single bond, —CH$_2$CH$_2$—, —CH$_2$O—, —COO—, —OCOO—, —N=N—, —CR$^a$=CR$^b$—, —C≡C— or —CR$^a$=N—, where R$^a$ and R$^b$ each independently represent a hydrogen atom or an alkyl group having 1 to 4 carbon atoms;
$U^1$ represents a hydrogen atom or a polymerizable group;
$U^2$ represents a polymerizable group;
$W^1$ and $W^2$ each independently represent a single bond, —O—, —S—, —COO— or —OCOO—; and
$V^1$ and $V^2$ each independently represent an alkanediyl group having 1 to 20 carbon atoms and optionally having a substituent, and —CH$_2$— in the alkanediyl group may be substituted with —O—, —S— or —NH—).
<7> A composition including a polymerizable liquid crystal compound, and a compound represented by the following general formula (1):

[Chemical Formula 5]

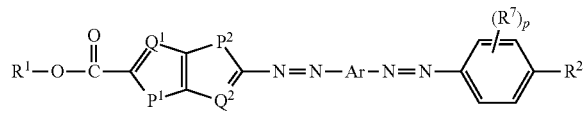

(1)

[in the general formula (1), $R^1$ represents an alkyl group having 1 to 11 carbon atoms;
$P^1$ and $P^2$ each independently represent —S—, —O— or —N(R$^{12}$)—, $R^{12}$ represents a hydrogen atom or an alkyl group having 1 to 4 carbon atoms, and $Q^1$ and $Q^2$ each independently represent =N— or =CH—;
Ar represents a group represented by the following general formula (Ar-1) or (Ar-2):

[Chemical Formula 6]

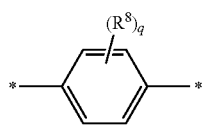
(Ar-1)

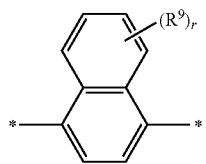
(Ar-2)

(in the above general formula, * represents a binding part with N);
$R^2$ represents a group selected from the following groups:

[Chemical Formula 7]

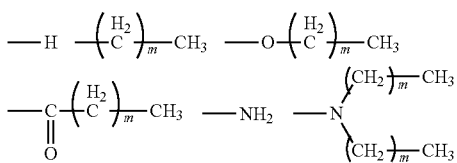

-continued

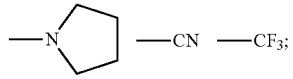

$R^7$ to $R^9$ are substituents other than a hydrogen atom, and each independently represent an alkyl group having 1 to 4 carbon atoms, an alkoxy group having 1 to 4 carbon atoms, a halogen atom or a cyano group, and one or more of hydrogen atoms in the alkyl group or the alkoxy group may be substituted with a halogen atom or a hydroxy group;
m represents an integer of 0 to 10, and when one group has two occurrences of m, the two occurrences of m may be mutually the same or different; and p, q and r each independently represent an integer of 0 to 2].
<8> The composition according to <7>, including two or more compounds which have mutually different structures and which are represented by the general formula (1).
<9> An optical film which is formed of the composition according to <7> or <8>.
<10> A circular polarizing plate including the optical film according to any one of <1> to <6> or <9>.
<11> A display device including the optical film according to any one of <1> to <6> or <9>.
<12> A compound represented by the following general formula (1):

[Chemical Formula 8]

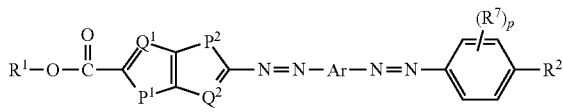

(1)

[in the general formula (1), represents an alkyl group having 1 to 11 carbon atoms;
$P^1$ and $P^2$ each independently represent —S—, —O— or —N(R$^{12}$)—, $R^{12}$ represents a hydrogen atom or an alkyl group having 1 to 4 carbon atoms, and $Q_1$ and $Q^2$ each independently represent =N— or =CH—;
Ar represents a group represented by the following general formula (Ar-1) or (Ar-2):

[Chemical Formula 9]

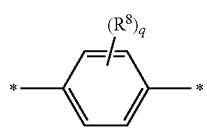
(Ar-1)

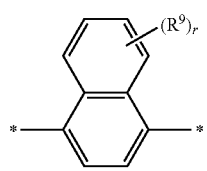
(Ar-2)

(in the above general formula, * represents a binding part with N);

$R^2$ represents a group selected from the following groups:

[Chemical Formula 10]

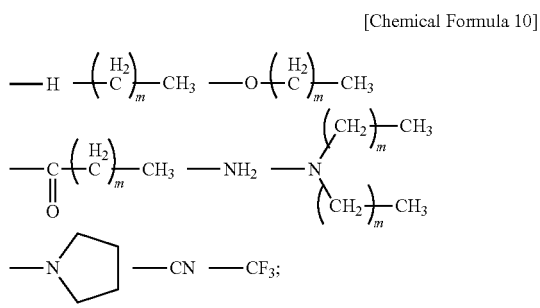

$R^7$ to $R^9$ are substituents other than a hydrogen atom, and each independently represent an alkyl group having 1 to 4 carbon atoms, an alkoxy group having 1 to 4 carbon atoms, a halogen atom or a cyano group, and one or more of hydrogen atoms in the alkyl group or the alkoxy group may be substituted with a halogen atom or a hydroxy group; m represents an integer of 0 to 10, and when one group has two occurrences of m, the two occurrences of m may be mutually the same or different; and p, q and r each independently represent an integer of 0 to 2].

<13> A method for producing a compound represented by the following general formula (1), the method including the step of reacting a compound represented by the following general formula (3), the following general formula (5) or the following general formula (6) and a compound represented by the following general formula ($R^1$-2):

[Chemical Formula 11]

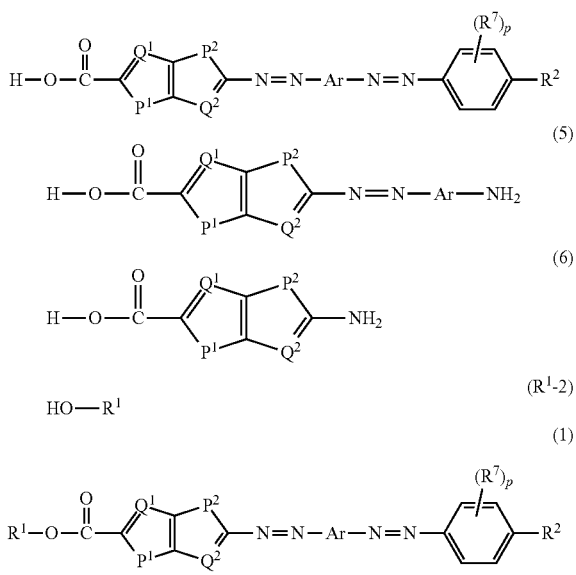

[in the above general formula, $R^1$ represents an alkyl group having 1 to 11 carbon atoms;
$P^1$ and $P^2$ each independently represent —S—, —O— or —N($R^{12}$)—, $R^{12}$ represents a hydrogen atom or an alkyl group having 1 to 4 carbon atoms, and $Q^1$ and $Q^2$ each independently represent =N— or =CH—;
Ar represents a group represented by the following general formula (Ar-1) or (Ar-2):

[Chemical Formula 12]

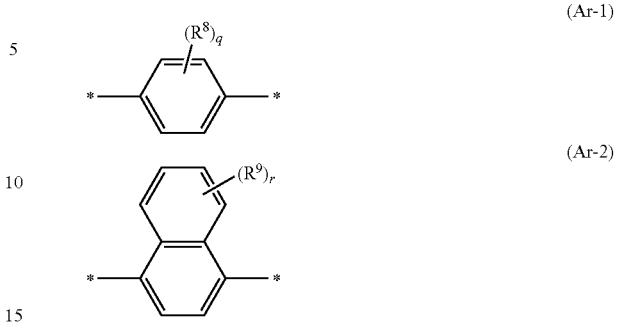

(in the above general formula, * represents a binding part with N);
$R^2$ represents a group selected from the following groups:

[Chemical Formula 13]

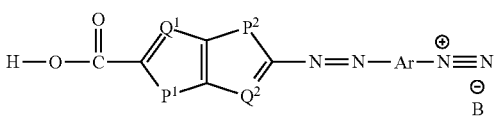

R⁷ to R⁹ are substituents other than a hydrogen atom, and each independently represent an alkyl group having 1 to 4 carbon atoms, an alkoxy group having 1 to 4 carbon atoms, a halogen atom or a cyano group, and one or more of hydrogen atoms in the alkyl group or the alkoxy group may be substituted with a halogen atom or a hydroxy group;
m represents an integer of 0 to 10, and when one group has two occurrences of m, the two occurrences of m may be mutually the same or different; and p, q and r each independently represent an integer of 0 to 2].

<14> The method for producing according to <13>, including the step of reacting a compound represented by the general formula (3), the general formula (5) or the general formula (6) and at least two compounds which have mutually different structures and which are represented by the general formula ($R^1$-2).

<15> A method for producing a compound represented by the following general formula (3), the method including reacting a compound represented by the following general formula (5-1) and a compound represented by the following general formula ($R^2$-1) in the presence of:
N-methylpyrrolidone, N, N-dimethylformamide, N, N-dimethylacetamide or dimethylsulfoxide:

[Chemical Formula 14]

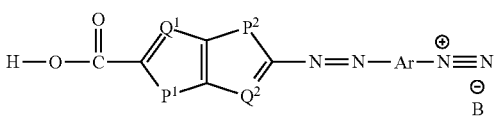

-continued

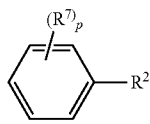
(R²-1)

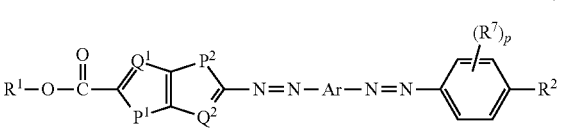
(3)

[in the above general formula, and P² each independently represent —S—, —O— or —N(R¹²) R¹² represents a hydrogen atom or an alkyl group having 1 to 4 carbon atoms, and Q¹ and Q² each independently represent =N— or =CH—;
B⁻ represents an anion; and
Ar represents a group represented by the following general formula (Ar-1) or (Ar-2):

[Chemical Formula 15]

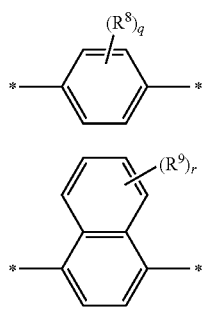

(Ar-1)

(Ar-2)

(in the above general formula, * represents a binding part with N);
R² represents a group selected from the following groups:

[Chemical Formula 16]

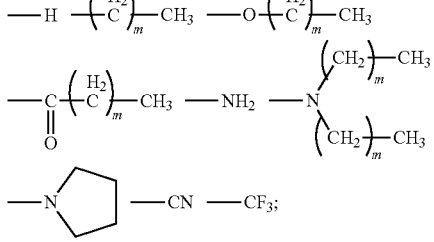

$R^7$ to $R^9$ are substituents other than a hydrogen atom, and each independently represent an alkyl group having 1 to 4 carbon atoms, an alkoxy group having 1 to 4 carbon atoms, a halogen atom or a cyano group, and one or more of hydrogen atoms in the alkyl group or the alkoxy group may be substituted with a halogen atom or a hydroxy group;
m represents an integer of 0 to 10, and when one group has two occurrences of m, the two occurrences of m may be mutually the same or different; and p, q and r each independently represent an integer of 0 to 2].

The optical film of the present invention is superior in light resistance to conventional optical films.

DETAILED DESCRIPTION OF THE PREFERRED EMBODIMENTS

Hereinafter, embodiments of the present invention will be described in detail. In the present application, "A to B" means "not less than A and not more than B".

Embodiment 1: Optical Film; and Embodiment 2: Composition

An optical film according to embodiment 1 of the present invention contains a compound represented by the following general formula (1) (hereinafter, also referred to as a compound (1)), and a polymer of a polymerizable liquid crystal compound. A composition according to embodiment 2 of the present invention contains the compound (1) and a polymerizable liquid crystal compound.

[Chemical Formula 17]

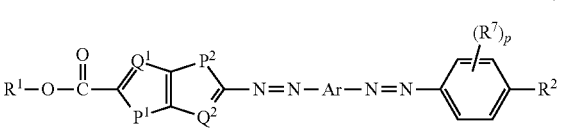
(1)

[in the general formula (1), $R^1$ represents an alkyl group having 1 to 11 carbon atoms;
$P^1$ and $P^2$ each independently represent —S—, —O— or —N(R¹²)—, $R^{12}$ represents a hydrogen atom or an alkyl group having 1 to 4 carbon atoms, and $Q^1$ and $Q^2$ each independently represent =N— or =CH—;
Ar represents a group represented by the following general formula (Ar-1) or (Ar-2):

[Chemical Formula 18]

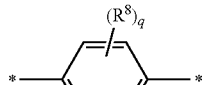
(Ar-1)

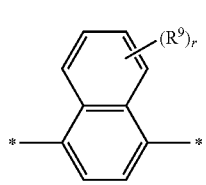
(Ar-2)

(in the above general formula, * represents a binding part with N);
$R^2$ represents a group selected from the following groups:

[Chemical Formula 19]

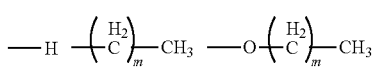

-continued

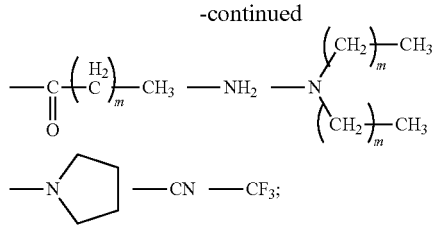

$R^7$ to $R^9$ are substituents other than a hydrogen atom, and each independently represent an alkyl group having 1 to 4 carbon atoms, an alkoxy group having 1 to 4 carbon atoms, a halogen atom or a cyano group, and one or more of hydrogen atoms in the alkyl group or the alkoxy group may be substituted with a halogen atom or a hydroxy group;
m represents an integer of 0 to 10, and when one group has two occurrences of m, the two occurrences of m may be mutually the same or different; and p, q and r each independently represent an integer of 0 to 2].

The optical film according to embodiment 1 of the present invention may be an optical film obtained by polymerizing (curing) a polymerizable liquid crystal compound in the composition according to embodiment 2 of the present invention. In other words, the optical film according to embodiment 1 of the present invention can be formed from the composition according to embodiment 2 of the present invention. Specifically, the optical film of the present invention can be obtained usually by applying the composition of the present invention, which contains a polymerizable liquid crystal compound, onto a base material or an orientation film formed on the base material, and polymerizing the polymerizable liquid crystal compound in the composition.

The optical film of the present invention may be, for example, a polarizing film. The optical film of the present invention is preferably a liquid crystal cured film with a polymerizable liquid crystal compound cured in an oriented state, more preferably a liquid crystal cured film with a polymerizable liquid crystal compound cured in a state of being oriented in a horizontal or perpendicular direction with respect to a base material surface.

A polarizing film containing the compound (1) serving as a dichroic dye can be formed from the composition of the present invention by polymerizing the polymerizable liquid crystal compound in the composition.

Components that may be contained in the composition of the present invention will be described below. Components that may be contained in the optical film of the present invention are the same as the components that may be contained in the composition of the present invention except that a polymer of the polymerizable liquid crystal compound is contained in place of the polymerizable liquid crystal compound. The content of the polymer of the polymerizable liquid crystal compound is described in terms of the amount of the polymerizable liquid crystal compound before polymerization thereof.

<Dichroic Dye>

The compound (1) in the present invention serves as a dichroic dye, and usually has an absorption at a wavelength in the range of 400 to 800 nm.

The positional isomers at the azobenzene part of the compound (1) are preferably trans-isomers.

Examples of the group $R^1$, i.e. an alkyl group having 1 to 11 carbon atoms, in the compound (1) include linear or branched alkyl groups having no substituent, such as a methyl group, an ethyl group, a n-propyl group, an isopropyl group, a n-butyl group, an isobutyl group, a tert-butyl group, a n-pentyl group, an isopentyl group, a neopentyl group, a n-hexyl group, a n-heptyl group, a n-octyl group, a n-nonyl group and a n-decyl group.

Examples of the group i.e. an alkyl group having 1 to 4 carbon atoms, in the compound (1) include linear or branched alkyl groups having no substituent, such as a methyl group, an ethyl group, a n-propyl group, an isopropyl group, a n-butyl group, an isobutyl group and a tert-butyl group.

$P^1$ and $P^2$ in the compound (1) are each preferably —S—. $Q^1$ and $Q^2$ in the compound (1) are preferably =CH— for $Q^1$ and =N— for $Q^2$. Thus, the compound (1) is more preferably a compound represented by the following general formula (2) (hereinafter, also referred to as a compound (2)).

[Chemical Formula 20]

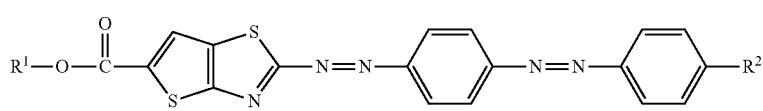

(2)

[in the general formula (2), $R^1$ and $R^2$ have the same meaning as $R^1$ and $R^2$ in the general formula (1)].

$R^7$ to $R^9$ in the compound (1) are substituents other than a hydrogen atom, and each independently represent an alkyl group having 1 to 4 carbon atoms, an alkoxy group having 1 to 4 carbon atoms, a halogen atom or a cyano group. The aromatic group in the compound (1) may be substituted at any position with $R^7$ to $R^9$.

Examples of the alkyl group having 1 to 4 carbon atoms, in the compound (1) include linear or branched alkyl groups having no substituent, such as a methyl group, an ethyl group, a n-propyl group, an isopropyl group, a n-butyl group, an isobutyl group and a tert-butyl group.

One or more of hydrogen atoms in the alkyl group having 1 to 4 carbon atoms may be substituted with a halogen atom (i.e. a fluorine atom) or a hydroxy group. Examples of the alkyl group in which one or more of hydrogen atoms is substituted with a halogen atom etc. include haloalkyl groups having 1 to 4 carbon atoms, such as a fluoromethyl group, a trifluoromethyl group, a pentafluoroethyl group and a nonafluorobutyl group; and hydroxyalkyl groups having 1 to 4 carbon atoms, such as a hydroxymethyl group and a 2-hydroxyethyl group.

Examples of the alkoxy group having 1 to 4 carbon atoms include linear or branched alkoxy groups having no substituent, such as a methoxy group, an ethoxy group, a n-propoxy group, an isopropoxy group, a n-butoxy group, an isobutoxy group and a tert-butoxy group.

One or more of hydrogen atoms in the alkoxy group having 1 to 4 carbon atoms may be substituted with a halogen atom (e.g. a fluorine atom) or a hydroxy group.

Examples of the alkoxy group in which one or more of hydrogen atoms is substituted with a halogen atom etc. include haloalkoxy groups having 1 to 4 carbon atoms, such as a fluoromethoxy group, a trifluoromethoxy group, a pentafluoroethoxy group and a nonafluorobutoxy group; and hydroxyalkoxy groups having 1 to 4 carbon atoms, such as a hydroxymethoxy group and a 2-hydroxyethoxy group.

p, q and r in the general formula (1) are each independently an integer of 0 to 2, preferably 0.

$R^2$ in the compound (1) is a group selected from the following groups.

[Chemical Formula 21]

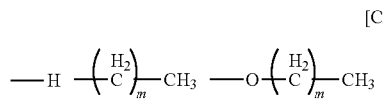

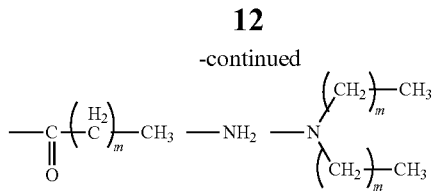

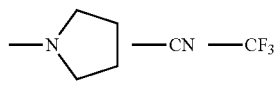

In particular, $R^2$ is more preferably —$N(CH_2$—$CH_3)_2$.

Specific examples of the compound (1) include compounds represented by the following formulae (1-1) to (1-34).

[Chemical Formula 22]

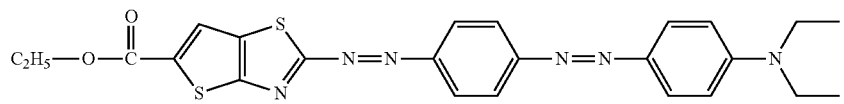
(1-1)

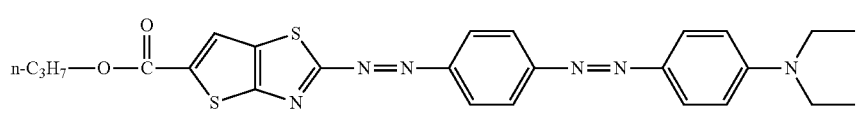
(1-2)

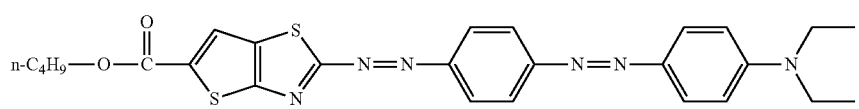
(1-3)

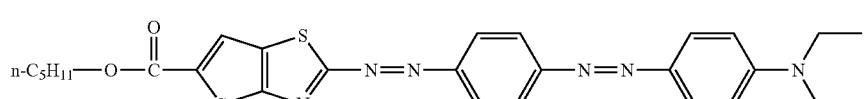
(1-4)

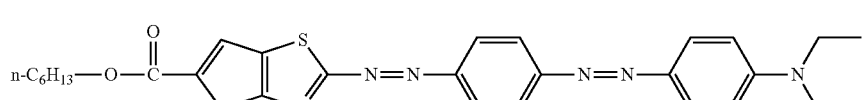
(1-5)

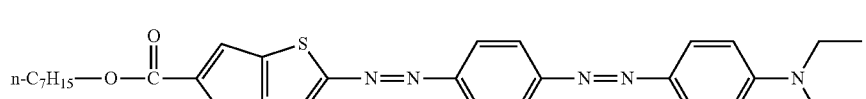
(1-6)

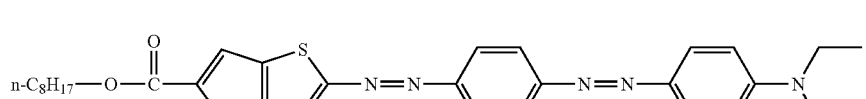
(1-7)

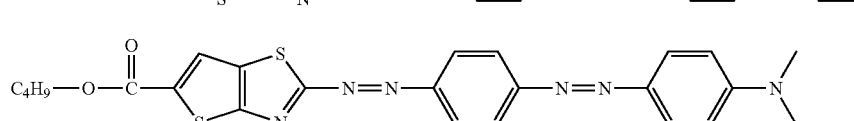
(1-8)

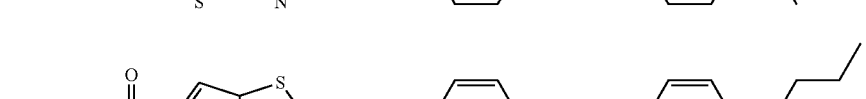
(1-9)

-continued
(1-10)
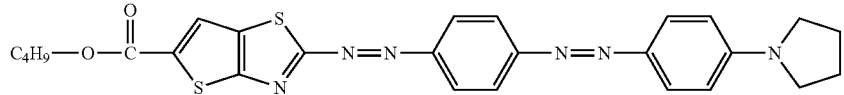
(1-11)
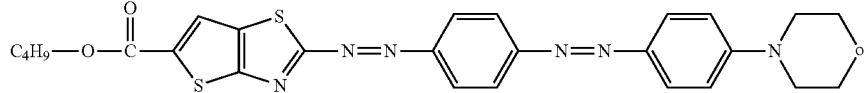
(1-12)
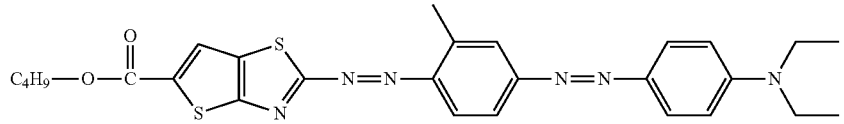
(1-13)
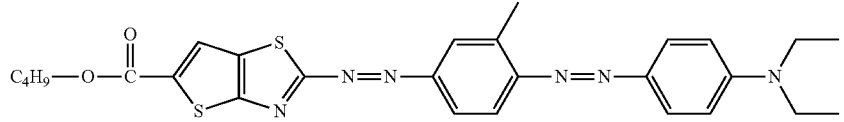
(1-14)
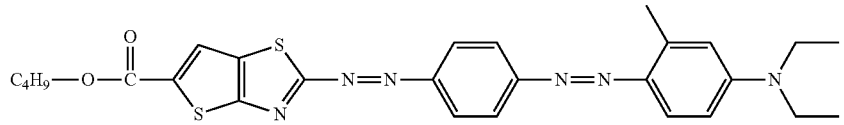
(1-15)
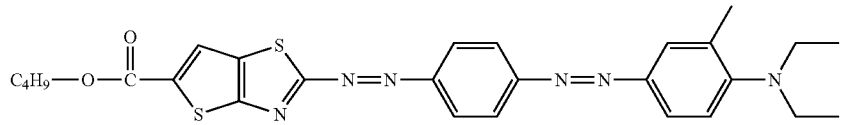
(1-16)
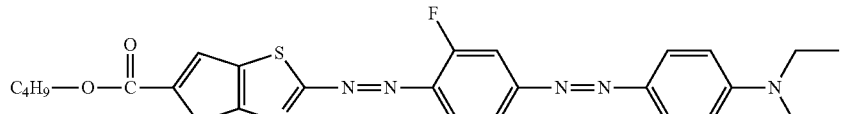
(1-17)
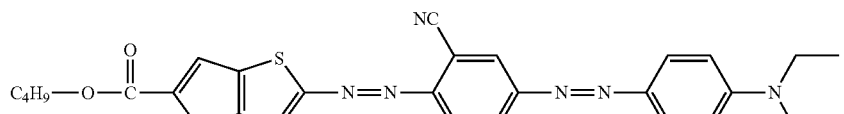
(1-18)
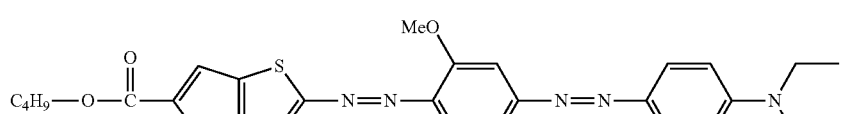
(1-19)
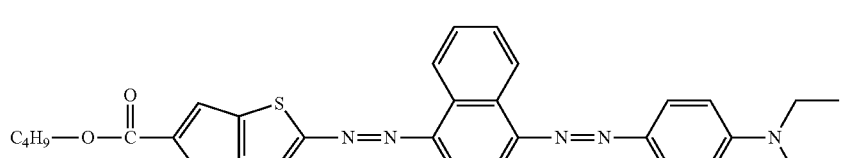
(1-20)
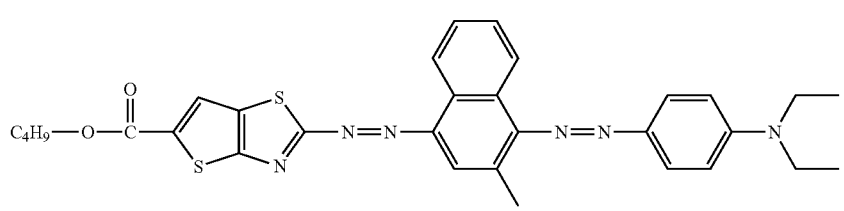

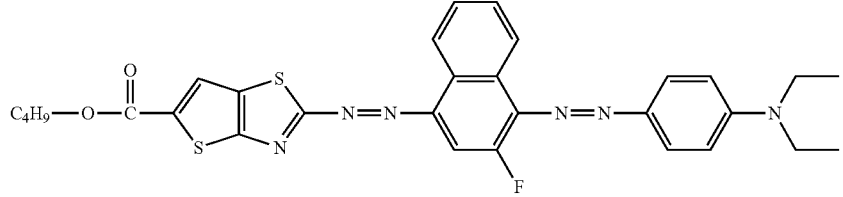
(1-21)
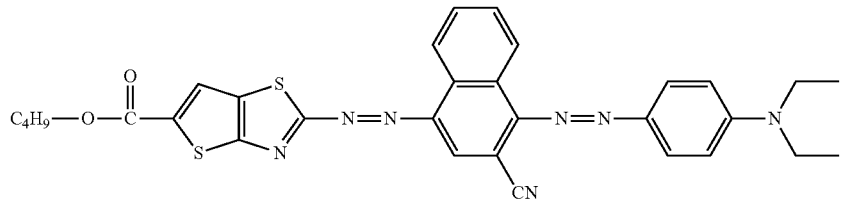
(1-22)
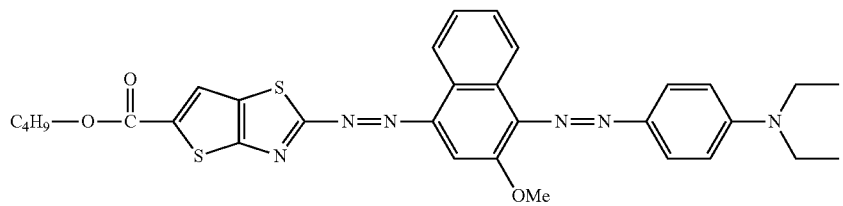
(1-23)
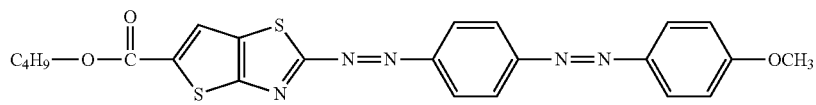
(1-24)
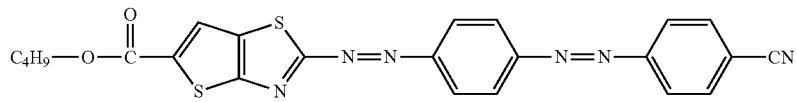
(1-25)
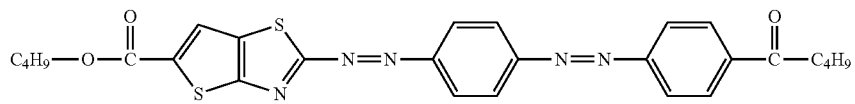
(1-26)
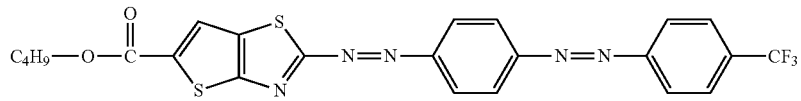
(1-27)
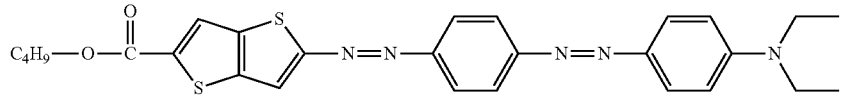
(1-28)
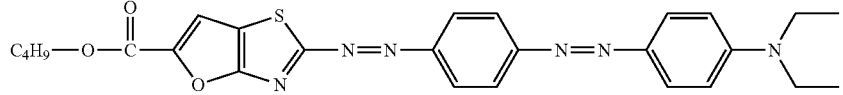
(1-29)
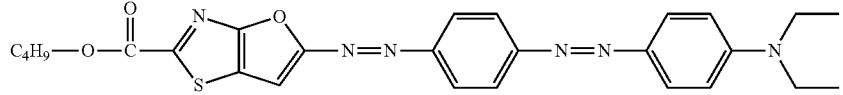
(1-30)
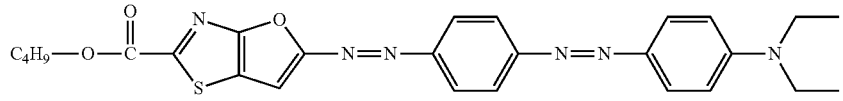
(1-31)

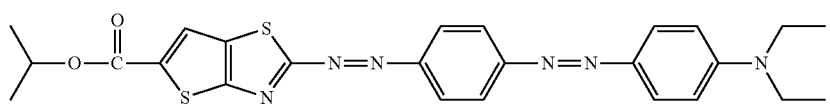

(1-32)

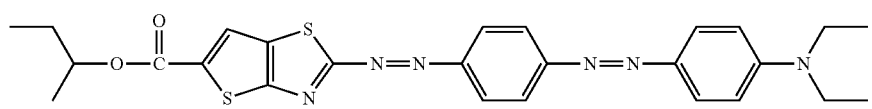

(1-33)

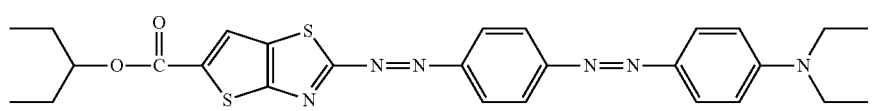

(1-34)

The compound (1) contained in the optical film of the present invention or the composition of the present invention is preferably a compound selected from compounds represented by the formulae (1-1), (1-2), (1-3), (1-4), (1-5), (1-6) and (1-7), more preferably a compound selected from compounds represented by the formulae (1-3) and (1-5), among the above-mentioned specific examples of the compound (1).

The compound (1) contained in the optical film of the present invention or the composition of the present invention may be a single compound, or a mixture of two or more compounds (1) having mutually different structures. It is preferred that the optical film or the composition contains two or more compounds (1) having mutually different structures for ensuring that the stability of the composition of the present invention can be improved, and as a result, productivity of the optical film of the present invention can be improved.

This may be because when the optical film or the composition contains two or more compounds (1), the compounds (1) are hardly crystallized and compatibility (solubility) of the compounds (1) is thus improved in the composition of the present invention, resulting in improvement of the stability of the composition of the present invention.

As two or more compounds (1) having mutually different structures, a mixture of compounds (1) having mutually different groups as $R^1$ and having the same structure at a part other than $R^1$ is preferred for ensuring that the effect of improving the stability can be exhibited, and two or more compounds (1) having mutually different structures can be easily prepared.

The compound (1) can be synthesized by a previously known synthesis method. Preferably, the compound (1) is produced by a method for producing a compound represented by the general formula (1) according to the present invention as described later.

The content of the compound (1) according to the present invention is preferably 50 parts by mass or less, more preferably not less than 0.1 parts by mass and not more than 20 parts by mass, still more preferably not less than 0.1 parts by mass and not more than 10 parts by mass in terms of a content based on 100 parts by mass of the later described polymerizable liquid crystal compound in the composition of the present invention. It is preferred that the content is within the above-mentioned range for ensuring that when the optical film of the present invention is formed using the composition of the present invention, i.e. when the polymerizable liquid crystal compound in the composition is polymerized, the orientation thereof is not disordered. When the optical film or the composition of the present invention contains two or more compounds (1), the total amount of the compounds (1) may in the above-mentioned range.

The content of the compound (1) in the optical film of the present invention is preferably in the same range as the above-mentioned preferred range for the composition of the present invention in terms of a content where the mass of a polymer of the polymerizable liquid crystal compound in the optical film of the present invention is converted into the mass of the polymerizable liquid crystal compound before polymerization, and then set to 100 parts by mass.

<Polymerizable Liquid Crystal Compound>

The polymerizable liquid crystal compound is a compound which has a polymerizable group in the molecule, and can be oriented to show a liquid crystal phase. The polymerizable liquid crystal compound is preferably a compound which can be singly oriented to show a liquid crystal phase.

The polymerizable group means a group which is involved in a polymerization reaction, and the polymerizable group is preferably a photopolymerizable group. Here, the polymerizable group is a group which can be involved in a polymerization reaction by active radicals, acids and the like generated from a polymerization initiator as described later. Examples of the polymerizable group include a vinyl group, a vinyloxy group, a 1-chlorovinyl group, an isopropenyl group, a 4-vinylphenyl group, an acryloyloxy group, a methacryloyloxy group, an oxiranyl group and an oxetanyl group. Among them, an acryloyloxy group, a methacryloyloxy group, a vinyloxy group, an oxiranyl group and an oxetanyl group are preferred, and an acryloyloxy group is more preferred.

The polymerizable liquid crystal compound may be a thermotropic liquid crystal-type compound, or a lyotropic liquid crystal-type compound.

The polymerizable liquid crystal compound in the present invention is preferably a smectic liquid crystal compound showing a smectic liquid crystal phase, more preferably a high-order smectic liquid crystal compound showing a high-order smectic liquid crystal phase. The composition of the present invention which contains a polymerizable liquid crystal compound showing a smectic liquid crystal phase is capable of giving a polarizing film (optical film) that is superior in polarizing performance. The composition of the present invention may contain two or more polymerizable liquid crystal compounds.

The compound (1) can exhibit high dichroism even in a state of being dispersed among dense molecular chains formed from the polymerizable liquid crystal compound showing a smectic liquid crystal phase. Thus, the composition of the present invention which contains the compound (1) can be used for formation of a polarizing film (optical film) having a high dichroic ratio.

Examples of the high-order smectic liquid crystal phase include a smectic B phase, a smectic D phase, a smectic E phase, a smectic F phase, a smectic G phase, a smectic H phase, a smectic I phase, a smectic J phase, a smectic K phase and a smectic L phase. Among them, a smectic B phase, a smectic F phase and a smectic I phase are preferred, and a smectic B phase is more preferred. When the smectic liquid crystal phase shown by the polymerizable liquid crystal compound is such a high-order smectic phase, a polarizing film (optical film) having a higher orientation order degree is obtained. A polarizing film (optical film) obtained from a composition containing a polymerizable liquid crystal compound showing a high-order smectic liquid crystal phase having a high orientation order degree shows a Bragg peak derived from a high-order structure such as a hexatic phase or a crystal phase in X-ray diffraction measurement. The Bragg peak is a peak derived from a surface periodic structure of molecular orientation. The periodic interval (order period) of a polarizing film (optical film) obtained from the composition of the present invention is preferably 0.30 to 0.50 nm.

The kind of the liquid crystal phase shown by the polymerizable liquid crystal compound can be confirmed by the method described below. An appropriate base material is provided, a solution containing a polymerizable liquid crystal compound and a solvent is applied to the base material to form a coating film on the base material, and a heating treatment or decompression treatment is then performed to remove a solvent contained in the coating film. Subsequently, the coating film formed on the base material is heated to an isotropic phase temperature, and then gradually cooled to develop a liquid crystal phase, and the liquid crystal phase is examined by texture observation with a polarizing microscope, X-ray diffraction measurement or differential scanning calorimetry. In the examination, for example, it can be confirmed that the polymerizable liquid crystal compound shows a nematic liquid crystal phase when cooled to a first temperature, and shows a smectic liquid crystal phase when further cooled to a second temperature gradually.

The polymerizable liquid crystal composition is preferably a compound represented by the formula (4) (hereinafter, also referred to as a "compound (4)".

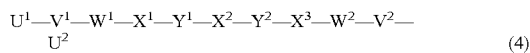
(4)

(in the formula, $X^1$, $X^2$ and $X^3$ each independently represent a 1,4-phenylene group optionally having a substituent, or a cyclohexane-1,4-diyl group optionally having a substituent, with the proviso that at least one of $X^1$, $X^2$ and $X^3$ is a 1,4-phenylene group optionally having a substituent, and —$CH_2$— in the cyclohexane-1,4-diyl group may be substituted with —O—, —S— or —NR—, where R represents an alkyl group having 1 to 6 carbon atoms, or a phenyl group;
$Y^1$ and $Y^2$ each independently represent a single bond, —$CH_2CH_2$—, —$CH_2O$—, —COO—, —OCOO—, —N=N—, —$CR^a$=$CR^b$—, —C≡C— or —$CR^a$=N—, where $R^a$ and $R^b$ each independently represent a hydrogen atom or an alkyl group having 1 to 4 carbon atoms;
$U^1$ represents a hydrogen atom or a polymerizable group;
$U^2$ represents a polymerizable group;
$W^1$ and $W^2$ each independently represent a single bond, —O—, —S—, —COO— or —OCOO—; and $V^1$ and $V^2$ each independently represent an alkanediyl group having 1 to 20 carbon atoms and optionally having a substituent, and —$CH_2$— in the alkanediyl group may be substituted with —O—, —S— or —NH—).

In the compound (4), at least one of $X^1$, $X^2$ and $X^3$ is a 1,4-phenylene group optionally having a substituent.

The 1,4-phenylene group optionally having a substituent is preferably a 1,4-phenylene group having no substituent. The cyclohexane-1,4-diyl group optionally having a substituent is preferably a trans-cyclohexane-1,4-diyl group optionally having a substituent. The trans-cyclohexane-1,4-diyl group optionally having a substituent is preferably a trans-cyclohexane-1,4-diyl group having no substituent.

Examples of the optional substituent in the 1,4-phenylene group optionally having a substituent or the cyclohexane-1,4-diyl group optionally having a substituent include alkyl groups having 1 to 4 carbon atoms, such as a methyl group, an ethyl group and a n-butyl group; a cyano group; and a halogen atom.

$Y^1$ is preferably a single bond, —$CH_2CH$— or —COO—, and $Y^2$ is preferably —$CH_2CH_2$— or —$CH_2O$—.

$U^1$ is a hydrogen atom or a polymerizable group, preferably a polymerizable group. $U^2$ is a polymerizable group. $U^1$ and $U^2$ are each preferably a polymerizable group, more preferably a photopolymerizable group. The polymerizable liquid crystal compound having a photopolymerizable group is advantageous because it can be polymerized under a lower temperature condition.

The polymerizable groups represented by $U^1$ and $U^2$ may be mutually different, but they are preferably the same. Examples of the polymerizable group include a vinyl group, a vinyloxy group, a 1-chlorovinyl group, an isopropenyl group, a 4-vinylphenyl group, an acryloyloxy group, a methacryloyloxy group, an oxiranyl group and an oxetanyl group. Among them, a vinyloxy group, an acryloyloxy group, a methacryloyloxy group, an oxiranyl group and an oxetanyl group are preferred, and an acryloyloxy group is more preferred.

Examples of the alkanediyl group represented by $V^1$ or $V^2$ include a methylene group, an ethylene group, a propane-1,3-diyl group, a butane-1,3-diyl group, a butane-1,4-diyl group, a pentane-1,5-diyl group, a hexane-1,6-diyl group, a heptane-1,7-diyl group, an octane-1,8-diyl group, a decane-1,10-diyl group, a tetradecane-1,14-diyl group and an icosane-1,20-diyl group. $V^1$ and $V^2$ are each preferably an alkanediyl group having 2 to 12 carbon atoms, more preferably an alkanediyl group having 6 to 12 carbon atoms.

Examples of the optional substituent in the alkanediyl group having 1 to 20 carbon atoms and optionally having a substituent include a cyano group and a halogen atom. The alkanediyl group is preferably an alkanediyl group having no substituent, more preferably a linear alkanediyl group having no substituent.

Preferably, $W^1$ and $W^2$ are each independently a single bond or —O—.

Specific examples of the compound (4) include compounds represented by the following formulae (4-1) to (4-43). When the compound (4) has a cyclohexane-1,4-diyl group, the cyclohexane-1,4-diyl group is preferably a trans-type group.

[Chemical Formula 23]
(4-1)
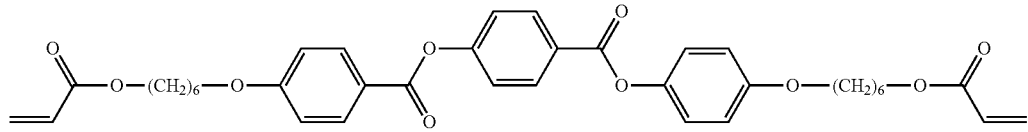
(4-2)
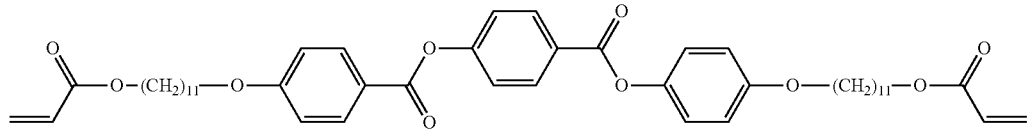
(4-3)
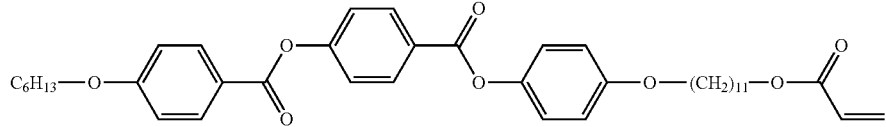
(4-4)
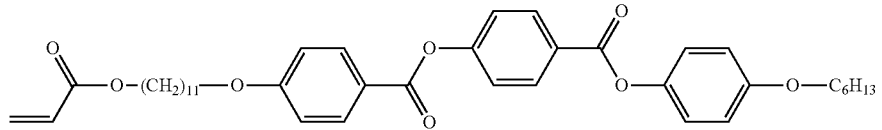
(4-5)
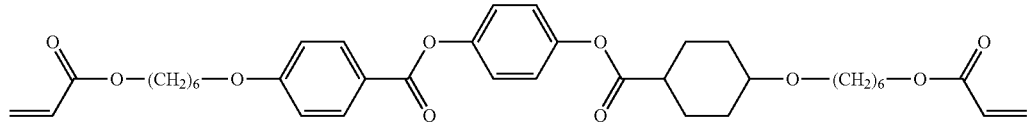
(4-6)
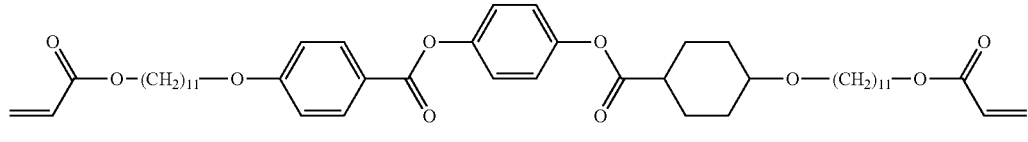
(4-7)
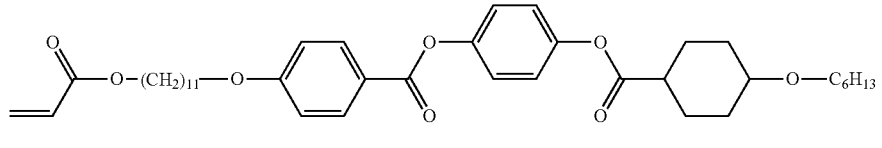
(4-8)
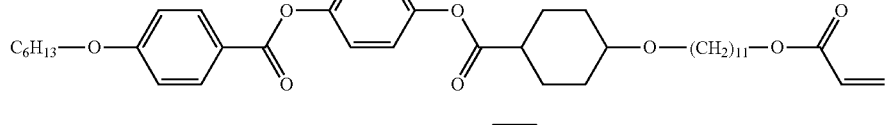
(4-9)
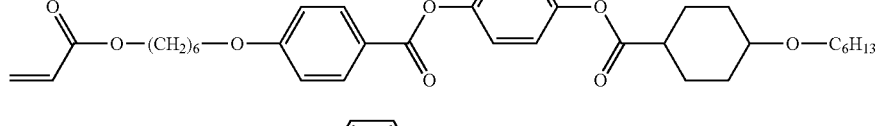
(4-10)
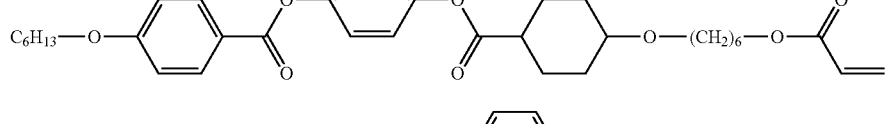
(4-11)
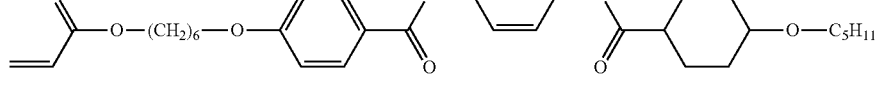

-continued
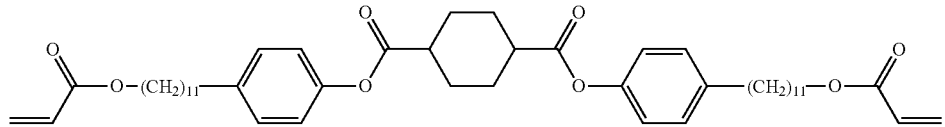
(4-12)
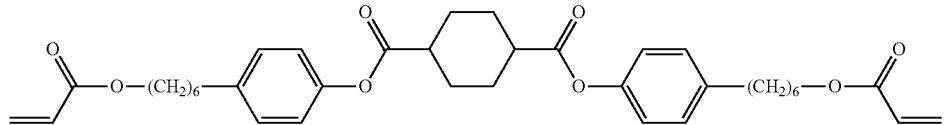
(4-13)
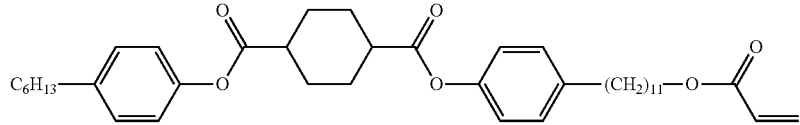
(4-14)
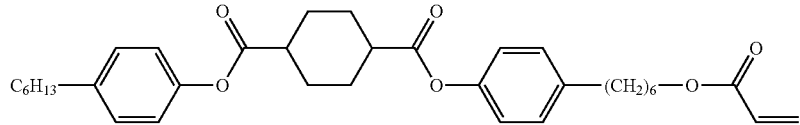
(4-15)
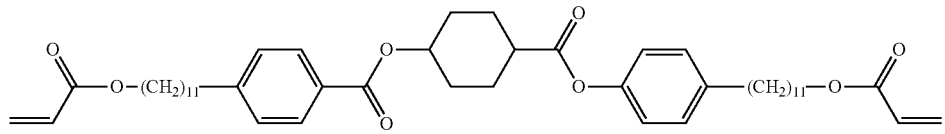
(4-16)
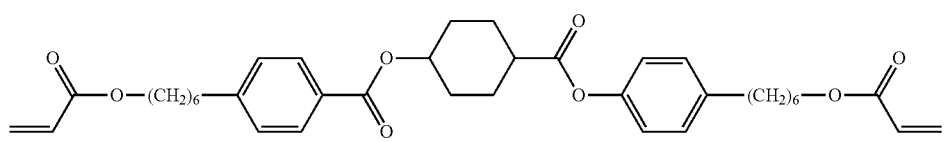
(4-17)
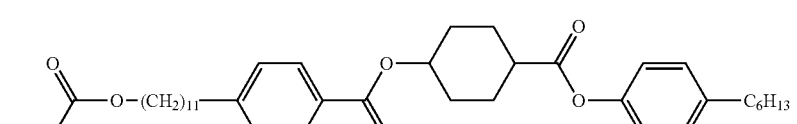
(4-18)
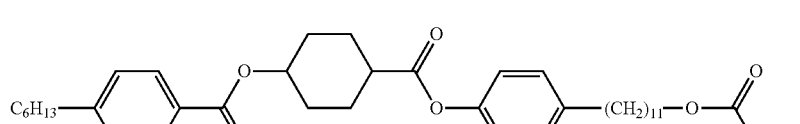
(4-19)
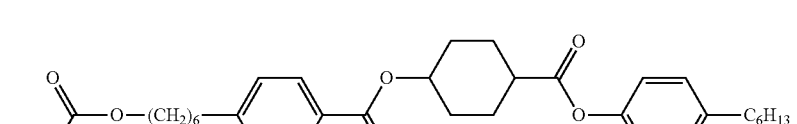
(4-20)
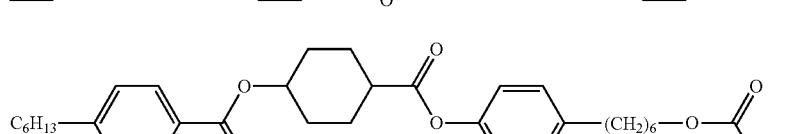
(4-21)
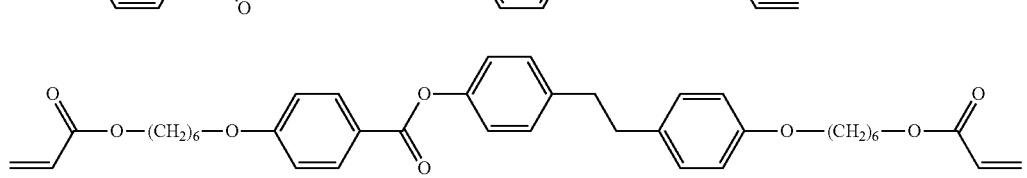
(4-22)

-continued
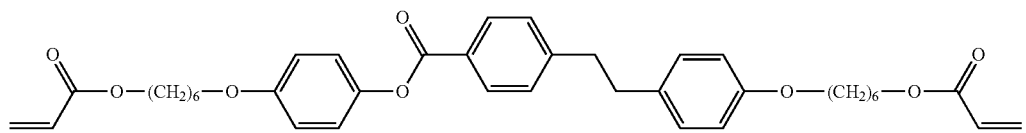
(4-23)
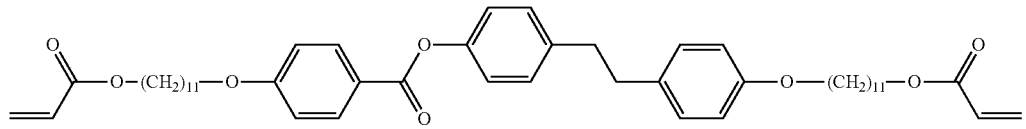
(4-24)
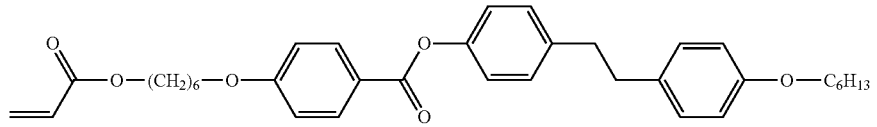
(4-25)
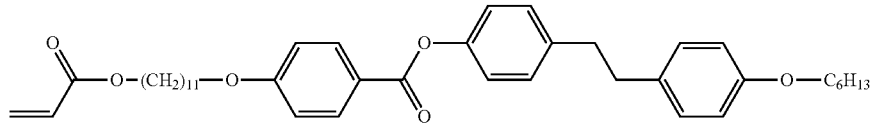
(4-26)
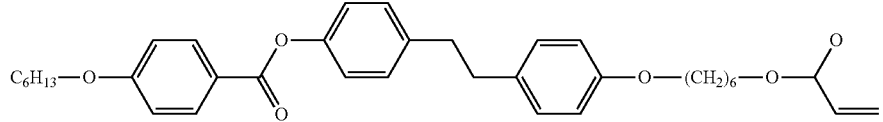
(4-27)
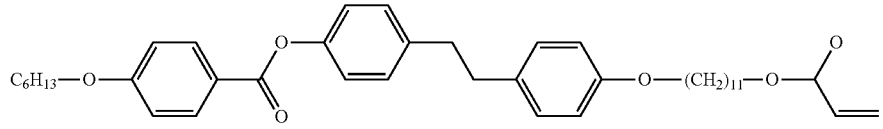
(4-28)
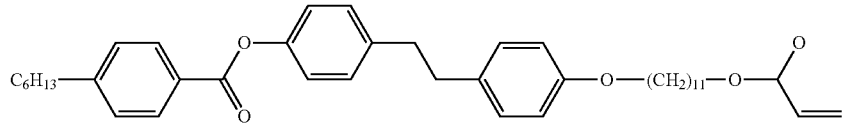
(4-29)
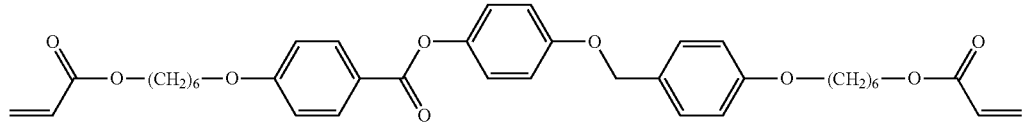
(4-30)
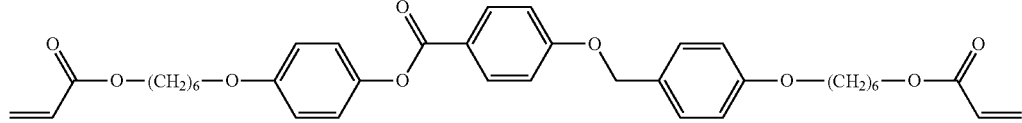
(4-31)
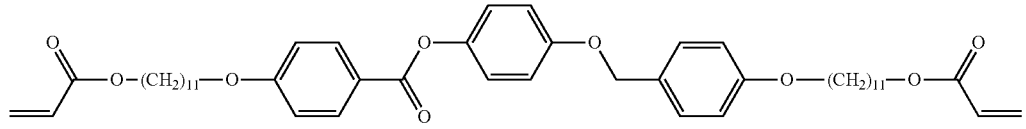
(4-32)
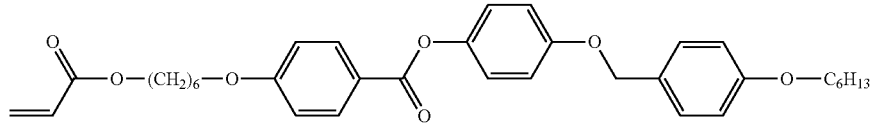
(4-33)

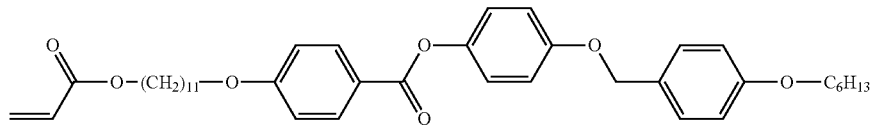
(4-34)

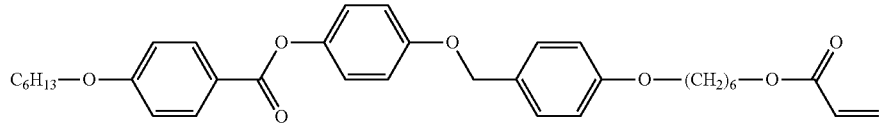
(4-35)

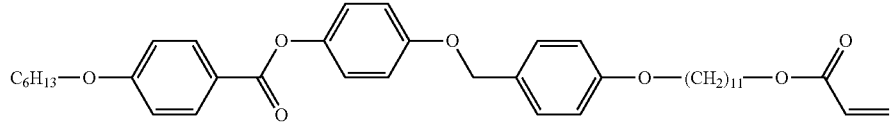
(4-36)

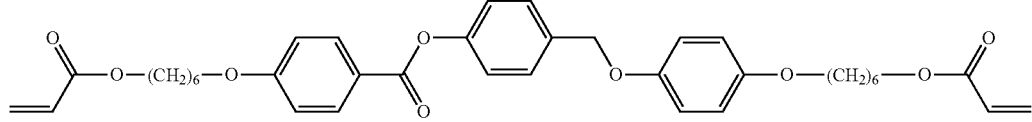
(4-37)

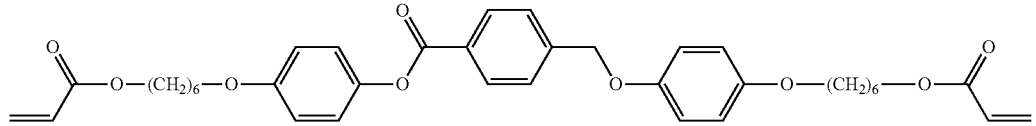
(4-38)

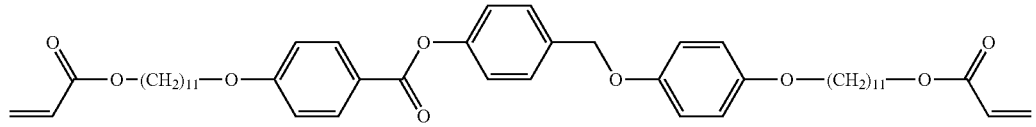
(4-39)

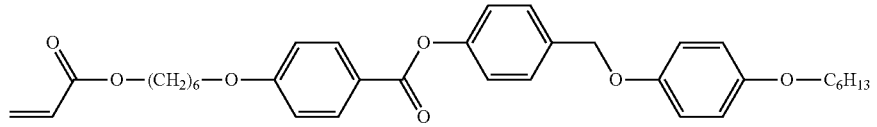
(4-40)

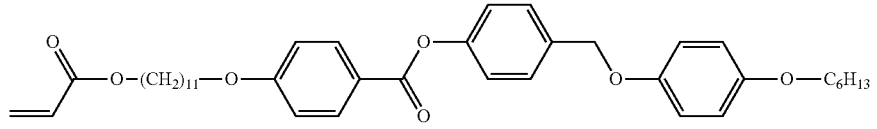
(4-41)

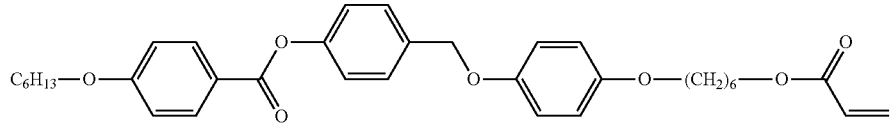
(4-42)

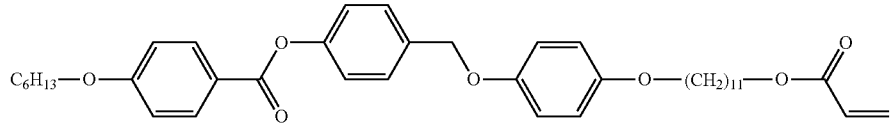
(4-43)

Among the above-mentioned specific examples of the polymerizable liquid crystal compound, at least one compound (4) selected from the group consisting of the compounds represented by the formulae (4-5), (4-6), (4-7), (4-8), (4-9), (4-10), (4-11), (4-12), (4-13), (4-14), (4-15), (4-22), (4-24), (4-25), (4-26), (4-27), (4-28) and (4-29) is preferred.

The optical film of the present invention and the composition of the present invention may each contain two or more compounds (4). When two or more polymerizable liquid crystal compounds are combined, it is preferred that at least one of the polymerizable liquid crystal compounds is the compound (4), and it is more preferred that two or more of the polymerizable liquid crystal compounds are the compound (4). When two or more polymerizable liquid crystal compounds are combined, it may be able to temporarily retain the liquid crystal phase even at a temperature of not higher than a liquid crystal-crystal phase transition temperature. The mixing ratio in combination of two polymerizable liquid crystal compounds is usually 1:99 to 50:50, preferably 5:95 to 50:50, more preferably 10:90 to 50:50.

The compound (4) can be produced using a method as described in a known document such as, for example, Lub et al. Recl. Tray. Chim. Pays-Bas, 115, 321-328 (1996) or JP-B-4719156.

The content of the polymerizable liquid crystal compound in the composition of the present invention is preferably 70 to 99.5 parts by mass, more preferably 80 to 99 parts by mass, still more preferably 80 to 94 parts by mass, especially preferably 80 to 90 parts by mass based on 100 parts by mass of a solid in the composition of the present invention for improving the orientation property of the polymerizable liquid crystal compound. Here, the solid refers to the total amount of components other than a solvent in the composition of the present invention.

The content of the polymer of the polymerizable liquid crystal compound in the optical film of the present invention is preferably in the same range as the above-mentioned preferred range for the content of the polymerizable liquid crystal compound in the composition of the present invention where the mass of the polymer of the polymerizable liquid crystal compound is converted into the mass of the polymerizable liquid crystal compound.

The optical film of the present invention and the composition of the present invention preferably contain a polymerization initiator and a solvent, and may further contain a photosensitizer, a polymerization inhibitor and a leveling agent as necessary.

<Polymerization Initiator>

The polymerization initiator is a compound capable of initiating a polymerization reaction of the polymerizable liquid crystal compound. The polymerization initiator is preferably a photopolymerization initiator which generates active radicals under the action of light.

Examples of the polymerization initiator include benzoin compounds, benzophenone compounds, alkylphenone compounds, acylphosphine oxide compounds, triazine compounds, iodonium salts and sulfonium salts.

Examples of the benzoin compound include benzoin, benzoin methyl ether, benzoin ethyl ether, benzoin isopropyl ether and benzoin isobutyl ether.

Examples of the benzophenone compound include benzophenone, methyl o-benzoylbenzoate 4-phenylbenzophenone, 4-benzoyl-4'-ethyldiphenyl sulfide, 3,3',4,4'-tetra(tert-butylperoxycarbonyl)benzophenone and 2,4,6-trimethylbenzophenone.

Examples of the alkylphenone compound include diethoxyacetophenone, 2-methyl-2-morphorino-1-(4-methylthiophenyl)propane-1-one, 2-benzyl-2-dimethylamino-1-(4-morphorinophenyl)butane-1-one, 2-hydroxy-2-methyl-1-phenylpropane-1-one, 1,2-diphenyl-2,2-dimethoxyethane-1-one, 2-hydroxy-2-methyl-1-[4-(2-hydroxyethoxy)phenyl]propane-1-one, 1-hydroxycyclohexylphenylketone, and oligomers of 2-hydroxy-2-methyl-1-[4-(1-methylvinyl)phenyl]propane-1-one.

Examples of the acylphosphine oxide compound include 2,4,6-trimethylbenzoyldiphenylphosphine oxide and bis(2,4,6-trimethylbenzoyl)phenylphosphine oxide.

Examples of the triazine compound include 2,4-bis(trichloromethyl)-6-(4-methoxyphenyl)-1,3,5-triazine, 2,4-bis(trichloromethyl)-6-(4-methoxynaphthyl)-1,3,5-triazine, 2,4-bis(trichloromethyl)-6-(4-methoxystyryl)-1,3,5-triazine, 2,4-bis(trichloromethyl)-6-[2-(5-methylfuran-2-yl)ethenyl]-1,3,5-triazine, 2,4-bis(trichloromethyl)-6-[2-(furan-2-yl) ethenyl]-1,3,5-triazine, 2,4-bis(trichloromethyl)-6-[2-(4-diethylamino-2-methylphenyl)etheynyl]-1,3,5-triazine and 2,4-bis(trichloromethyl)-6-[2-(3,4-dimethoxyphenyl)ethenyl]-1,3,5-triazine.

Examples of the iodonium salt or the sulfonium salt include salts represented by the following formulae.

[Chemical Formula 24]

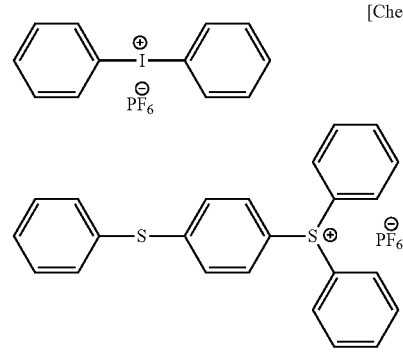

The polymerization initiators may be used alone, or in combination of two or more thereof.

As the polymerization initiator, a commercial product may be used. Examples of the commercially available polymerization initiator include IRGACURE (registered trademark) 907, 184, 651, 819, 250 and 369 (manufactured by Ciba Specialty Chemicals Inc.); SEIKUOL (registered trademark) BZ, Z and BEE (manufactured by Seiko Chemical Co., Ltd.); KAYACURE (registered trademark) BP100 and UVI-6992 (manufactured by The Dow Chemical Company); ADEKA OPTOMER SP-152 and SP-170 (manufactured by ADEKA CORPORATION); TAZ-A and TAZ-PP (manufactured by Nihon Siberhegner K.K.); and TAZ-104 (manufactured by Sanwa Chemical Co., Ltd.).

When the composition of the present invention contains a polymerization initiator, the content of the polymerization initiator in the composition of the present invention is usually 0.1 to 30 parts by mass, preferably 0.5 to 10 parts by mass, more preferably 0.5 to 8 parts by mass based on 100 parts by mass of the polymerizable liquid crystal compound for ensuring that the orientation of the polymerizable liquid crystal compound is hardly disordered. The content of the polymerization initiator in the optical film of the present invention is preferably in the same range as the above-mentioned preferred range for the content of the polymerization initiator in the composition of the present invention where the mass of the polymer of the polymerizable liquid crystal compound is converted into the mass of the polymerizable liquid crystal compound.

<Solvent>

The solvent is preferably a solvent capable of fully dissolving the polymerizable liquid crystal compound and the compound (1). Further, the solvent is preferably a solvent inactive to a polymerization reaction of the polymerizable liquid crystal compound.

Examples of the solvent include alcohol solvents such as methanol, ethanol, ethylene glycol, isopropyl alcohol, propylene glycol, ethylene glycol methyl ether, ethylene glycol butyl ether and propylene glycol monomethyl ether; ester solvents such as ethyl acetate, butyl acetate, ethylene glycol methyl ether acetate, γ-butyrolactone, propylene glycol methyl ether acetate and ethyl lactate; ketone solvents such as acetone, methyl ethyl ketone, cyclopentanone, cyclohexanone, 2-heptanone and methyl isobutyl ketone; aliphatic hydrocarbon solvents such as pentane, hexane and heptane; aromatic hydrocarbon solvents such as toluene and xylene; nitrile solvents such as acetonitrile; ether solvents such as tetrahydrofuran and dimethoxyethane; and chlorine-containing solvents such as chloroform and chlorobenzene. These solvents may be used alone, or in combination of two or more thereof.

The content of the solvent based on 100 parts by mass of the composition is preferably 50 parts by mass to 98 parts by mass. Thus, the content of the solid based on 100 parts by mass of the composition is preferably 2 parts by mass to 50 parts by mass. When the content of the solid in the composition is 50 parts by mass or less, the composition has a low viscosity, and therefore the resulting optical film has a uniform thickness, so that unevenness tends to hardly occur in the optical film. The content of the solid can be appropriately determined with consideration given to the thickness of an optical film to be produced.

Since a method for forming the optical film of the present invention usually includes a step of removing a solvent from a formed coating film by drying, the optical film of the present invention contains no solvent, or only a negligible amount of the solvent.

<Sensitizer>

By using a sensitizer, the polymerization reaction of the polymerizable liquid crystal compound can be further accelerated.

The sensitizer is preferably a photosensitizer particularly when the composition of the present invention contains a photopolymerization initiator. Examples of the sensitizer include xanthone compounds xanthone and thioxanthone (2,4-diethylthioxanthone, 2-isopropylthioxanthone and the like); anthracene compounds such as anthracene and alkoxy group-containing anthracene (such as dibutoxyanthracene); and phenothiazine and rubrene.

The content of the sensitizer in the composition is preferably 0.1 parts by mass to 30 parts by mass, more preferably 0.5 parts by mass to 10 parts by mass, still more preferably 0.5 parts by mass to 8 parts by mass based on 100 parts by mass of the polymerizable liquid crystal compound. The content of the sensitizer in the optical film of the present invention is preferably in the same range as the above-mentioned preferred range for the content of the sensitizer in the composition of the present invention where the mass of the polymer of the polymerizable liquid crystal compound is converted into the mass of the polymerizable liquid crystal compound.

<Polymerization Inhibitor>

By using a polymerization inhibitor, the degree of progression of the polymerization reaction of the polymerizable liquid crystal compound can be controlled.

Examples of the polymerization inhibitor include radical scavengers such as phenol-based compounds such as 2,6-di-tert-butyl-4-methylphenol; sulfur-based compounds such as dilauryl thiodipropionate; phosphorus-based compounds such as trioctyl phosphite; and amine-based compounds including a hindered amine structure as typified by 2,2,6,6-tetramethylpiperidine.

The polymerization inhibitor is preferably a phenol-based compound in that staining of the optical film as a liquid crystal cured film is reduced.

The content of the polymerization inhibitor in the composition is preferably 0.1 parts by mass to 30 parts by mass, more preferably 0.5 parts by mass to 10 parts by mass, still more preferably 0.5 parts by mass to 8 parts by mass based on 100 parts by mass of the polymerizable liquid crystal compound. When the content of the polymerization inhibitor is within the above-mentioned range, the polymerizable liquid crystal compound can be polymerized without disordering the orientation of the compound. The polymerization inhibitors may be used alone, or in combination of two or more thereof. The content of the polymerization inhibitor in the optical film of the present invention is preferably in the same range as the above-mentioned preferred range for the content of the polymerization inhibitor in the composition of the present invention where the mass of the polymer of the polymerizable liquid crystal compound is converted into the mass of the polymerizable liquid crystal compound.

<Leveling Agent>

The leveling agent is an additive which serves to adjust the fluidity of the composition, and further flatten a film obtained by applying the composition. Examples of the leveling agent include surfactants. Examples of the preferred leveling agent include leveling agents mainly composed of a polyacrylate compound, such as "BYK-361N" (manufactured by BYE Chemie GmbH); and leveling agents mainly composed of a fluorine atom-containing compound, such as Surflon (registered trademark) "S-381" (manufactured by AGC SEIMI CHEMICAL CO., LTD.).

The content of the leveling agent in the composition is preferably 0.01 parts by mass to 5 parts by mass, more preferably 0.1 parts by mass to 3 parts by mass based on 100 parts by mass of the polymerizable liquid crystal compound. When the content of the leveling agent is within the above-mentioned range, it is easy to horizontally orient the polymerizable liquid crystal compound, and the resulting optical film tends to be more smooth. The composition may contain two or more leveling agents. The content of the leveling agent in the optical film of the present invention is preferably in the same range as the above-mentioned preferred range for the content of the leveling agent in the composition of the present invention where the mass of the polymer of the polymerizable liquid crystal compound is converted into the mass of the polymerizable liquid crystal compound.

<Members of Optical Film>

The optical film of the present invention can be obtained usually by applying the composition of the present invention, which contains a polymerizable liquid crystal compound, onto a base material or an orientation film formed on the base material, and polymerizing the polymerizable liquid crystal compound in the composition.

Members for forming the optical film of the present invention, specifically a base material and an orientation film which are used in production of the optical film of the present invention.

<Base Material>

Examples of the base material include glass base materials and plastic base materials. Plastic base materials are preferred. Examples of the plastic for forming the plastic base material include plastics such as polyolefins such as polyethylene, polypropylene and norbornene-based polymers; cyclic olefin-based resins; polyvinyl alcohol; polyethylene terephthalate; polymethacrylic acid esters; polyacrylic acid esters; cellulose esters such as triacetyl cellulose, diacetyl cellulose and cellulose acetate propionate; polyethylene naphthalate; polycarbonate; polysulfone; polyether sulfone; polyether ketone; and polyphenylene sulfide and polyphenylene oxide.

Examples of the commercial available cellulose ester base material include "FUJITAC" (manufactured by Fuji Photo Film Co., Ltd.); and"KC8UX2M", "KC8UY" and "KC4UY" (manufactured by Konica Minolta Opto Co., Ltd.).

Examples of the commercially available cyclic olefin-based resin include "Topas" (registered trademark) (manufactured by Ticona Inc.); "ARTON" (registered trademark) (manufactured by JSR Corporation); "ZEONOR" (registered trademark) and "ZEONEX" (registered trademark) (manufactured by Zeon Corporation); and "APEL" (registered trademark") (manufactured by Mitsui Chemicals, Inc.). Abase material can be obtained by forming such a cyclic olefin-based resin into a film using a known method such as a solvent cast method or a melt-extruding method. A commercial available cyclic olefin-based resin base material can also be used. Examples of the commercial available cyclic olefin-based resin base material include "ESSINA" (registered trademark) and "SCA40" (registered trademark) (manufactured by Sekisui Chemical Company, Limited); "ZEONOR FILM" (registered trademark) (manufactured by Optes Inc.); and "ARTON FILM" (registered trademark) (manufactured by JSR Corporation).

The thickness of the base material is preferably small for the base material to have a mass suitable for practical handling, but when the thickness is excessively small, the strength tends to decrease, resulting in poor processability. The thickness of the base material is usually 5 μm to 300 μm, preferably 20 μm to 200 μm.

<Orientation Film>

The orientation film is a film having a thickness of 500 nm or less, and having an orientation regulating force for liquid-crystallographically orienting the polymerizable liquid crystal compound in a desired direction. Examples of the orientation film include orientation films formed of an orientational polymer, photo-orientation films and groove orientation films.

The orientation film facilitates the liquid crystal orientation of the polymerizable liquid crystal compound. The states of liquid crystal orientation such as a horizontal orientation, a perpendicular orientation, a hybrid orientation and an inclined orientation vary depending on the natures of the orientation film and the polymerizable liquid crystal compound, and a combination of the states of liquid crystal orientation can be arbitrarily selected. When the orientation film is a material which develops a horizontal orientation by an orientation regulation force, the polymerizable liquid crystal compound can form a horizontal orientation or a hybrid orientation. When the orientation film is a material which develops a perpendicular orientation, the polymerizable crystal compound can form a perpendicular orientation or an inclined orientation. The expressions of "horizontal", "perpendicular" and the like mentioned here refer to a direction of the major axis of the oriented polymerizable liquid crystal compound with the optical film (polarizing film) plane as a reference. The perpendicular orientation is an orientation including the major axis of the polymerizable liquid crystal compound oriented in a direction perpendicular to the optical film (polarizing film) plane. The term "perpendicular" mentioned here means an angle of 90°±20° with respect to the optical film (polarizing film) plane.

When the orientation film is formed of an orientational polymer, the orientation regulation force can be arbitrarily adjusted according to the surface state of the polymer and rubbing conditions. When the orientation film is formed of a photo-orientational polymer, the orientation regulation force can be arbitrarily adjusted according to conditions for irradiating the polymer with polarized light, etc. The liquid crystal orientation of the polymerizable liquid crystal compound can also be controlled by selecting physical properties such as a surface tension and liquid crystal properties of the polymerizable liquid crystal compound.

The orientation film formed between the base material and the optical film (polarizing film) is preferably a film which is insoluble in a solvent to be used in formation of the optical film (polarizing film) on the orientation film, and has heat resistance in heating treatment for removal of the solvent and orientation of a liquid crystal. Examples of the orientation film include orientation films formed of an orientational polymer, photo-orientation films and groove orientation films.

The thickness of the orientation film is usually 10 nm to 500 nm, preferably 10 nm to 200 nm.

<Orientation Film Formed of Orientational Polymer>

The orientation film formed of an orientational polymer is usually prepared in the following manner: a composition with an orientational polymer dissolved in a solvent (hereinafter, sometimes referred to as an orientational polymer composition) is applied to a base material, and the solvent is removed; or an orientational polymer composition is applied to a base material, the solvent is removed, and the applied orientational polymer composition is rubbed (rubbing method).

The concentration of the orientational polymer in the orientational polymer composition may be within a range which ensures that the orientational polymer material can be fully dissolved in the solvent, and the concentration of the orientational polymer is preferably 0.1% by mass to 20% by mass, more preferably 0.1% by mass to 10% by mass in terms of a solid content based on the amount of the solution.

Examples of the commercial available orientational polymer composition include SUNEVER (registered trademark) (manufactured by Nissan Chemical Industries, Limited) and OPTOMER (registered trademark) (manufactured by JSR Corporation).

<Photo-Orientation Film>

The photo-polymerization is usually prepared in the following manner: a composition containing a polymer or monomer (photo-orientational material) having a photoreactive group, and a solvent (herein after, the composition is sometimes referred to as a photo-orientation film forming composition) is applied to a base material, and irradiated with polarized light (preferably polarized UV light). The photo-orientation film is more preferred in the orientation regulation force can be arbitrarily controlled by selecting a polarization direction of polarized light to be applied.

The photoreactive group refers to a group which develops a liquid crystal orientation ability upon application of light. Specifically, the photoreactive group is a group which causes a photoreaction as an origin of the liquid crystal orientation ability, such as induction of orientation, or an isomerization reaction, a dimerization reaction, a photo-crosslinking or a photodegradation reaction of molecules generated upon application of light. Among such photoreactive groups, a group which causes a dimerization reaction or a photo-crosslinking reaction is preferred because it has an excellent orientation property. The photoreactive group which can cause the above-mentioned reaction is preferably a group having an unsaturated bond, particularly a double bond, especially preferably a group having at least unsaturated bond selected from the group consisting of a carbon-carbon double bond (C=C bond), a carbon-nitrogen double bond (C=N bond), a nitrogen-nitrogen double bond (N=N bond), and a carbon-oxygen double bond (C=O bond).

The content of the polymer or monomer having a photoreactive group, based on the amount of the photo-orientation film forming composition, is preferably 0.2% by mass or more, especially preferably 0.3% by mass to 10% by mass. The photo-orientation film forming composition may contain a high-molecular material such as polyvinyl alcohol or polyimide and a photosensitizer within the bounds of not significantly impairing the properties of the photo-orientation film.

For application of polarized light, the photo-orientation film forming composition applied on a substrate may be freed of a solvent, and directly irradiated with polarized light, or polarized light may be applied to the base material, and transmitted to irradiate the composition with polarized light. The polarized light is especially preferably substantially parallel light. The wavelength of the polarized light to be applied is preferably a wavelength in a wavelength range which ensures that the photoreactive group in the polymer or monomer having the photoreactive group can absorb light energy. Specifically, UV light (ultraviolet ray) having a wavelength of 250 nm to 400 nm is especially preferred.

When the composition is masked in rubbing or application of polarized light, a plurality of regions (patterns) different in direction of liquid crystal orientation.

<Groove Orientation Film>

The groove orientation film is a film having an irregularity pattern or a plurality of grooves on a film surface. When the polymerizable liquid crystal compound is applied to a film having a plurality of linear grooves arranged at equal intervals, liquid crystal molecules are oriented in a direction along the grooves.

Examples of the method for obtaining a groove orientation film include a method in which a photosensitive polyimide film surface is exposed through an exposure mask having a pattern-shaped slit, and the film is then developed and rinsed to form an irregularity pattern; a method in which a layer of UV-curable resin before curing is formed on an original board having a groove on a surface thereof, and the resin layer is transferred to a base material, and then cured; and a method in which a film of UV-curable resin before curing is formed on a base material, and a roll-shaped original board having a plurality of grooves is abut against the film to form irregularities, followed by curing the film. Specific examples of the method for obtaining a groove orientation film include methods described in JP-A-6-34976 and JP-A-2011-242743.

Examples of the method for applying the composition of the present invention include the same methods as those described above as examples of the method for applying the orientational polymer composition to the base material.

When the composition of the present invention contains a solvent, the solvent is usually removed from the formed coating film. Examples of method for removing the solvent include natural drying, forced-air drying, drying by heating and drying under reduced pressure.

The polymerizable liquid crystal compound contained in the formed coating film is usually oriented to form a liquid crystal phase when the film is heated to a temperature of not lower than a temperature at which the compound turns into a solution state, and the film is then cooled to a temperature at which the compound is liquid-crystallographically oriented.

The temperature at which the polymerizable liquid crystal compound contained in the formed coating film is oriented may be determined beforehand by, for example, observation of textures using a composition containing the polymerizable liquid crystal compound. The solvent may be removed concurrently with liquid crystal orientation. The temperature here depends on the kinds of a solvent to be removed, and a polymerizable liquid crystal compound, but is preferably in the range of 50 to 200° C., and more preferably in the range of 80 to 130° C. when the base material is a resin base material.

When a base material being a quarter-wave plate is used to obtain a circular polarizing plate including the optical film of the present invention and the quarter-wave plate, the orientation direction of the polymerizable liquid crystal compound may be set in such a manner that the transmission axis of the resulting optical film and the slow axis (optical axis) of the base material form an angle of substantially 45°.

The polymerizable liquid crystal compound is polymerized by irradiating the oriented polymerizable liquid crystal compound with an active energy ray.

The oriented polymerizable liquid crystal compound is polymerized to obtain an optical film containing the polymerizable liquid crystal compound polymerized in an oriented state, and the compound (1) oriented along with the polymerizable liquid crystal compound.

A polarizing film (optical film) containing a polymerizable liquid crystal compound polymerized while retaining a smectic liquid crystal phase has higher polarizing performance as compared to a conventional host-guest-type polarizing film, i.e. a polarizing film obtained by polymerizing a polymerizable liquid crystal compound etc. while retaining a nematic liquid crystal phase, and is superior in polarizing performance and strength to a polarizing film obtained by applying only a dichroic dye or a liquid crystal compound of lyotropic liquid crystal type.

The light source of an active energy ray may be a light source which generates an ultraviolet ray, an electron beam, an X-ray or the like. The light source is preferably a light source having a light emission distribution at a wavelength of 400 nm or less, such as a low-pressure mercury lamp, a middle-pressure mercury lamp, a high-pressure mercury lamp, an ultra-high-pressure mercury lamp, a chemical lamp, a black light lamp, a microwave-excited mercury lamp or a metal halide lamp.

The irradiation energy of the active energy ray is set to preferably 10 to 5000 mJ/cm$^2$, more preferably 100 to 2000 mJ/cm$^2$ in terms of an irradiation intensity in a wavelength range effective for activation of a polymerization initiator. When the irradiation energy is lower than 10 mJ/cm$^2$, curing of the polymerizable liquid crystal compound tends to be insufficient.

The thickness of the thus-formed optical film of the present invention is preferably not less than 0.5 µm and not more than 10 µm, more preferably not less than 1 µm and not more than 5 µm. The thickness of the optical film of the present invention can be determined by measurement using an interference thickness meter, a laser microscope or a contact-type thickness meter.

The optical film of the present invention is especially preferably an optical film in which a Bragg peak is obtained in X-ray diffraction measurement. The optical film of the present invention in which such a Bragg peak is obtained is, for example, a polarizing film which shows a diffraction peak derived from a hexatic phase or a crystal phase.

The maximum absorption in the optical film of the present invention exists preferably in the range of 350 nm to 550 nm, more preferably in the range of 430 nm to 550 nm. Preferably, the maximum absorption $\mu_{max1}$ is shifted to a longer wavelength as compared to the maximum absorption ($\lambda_{max2}$) measured using an appropriate solvent in which the compound (1) contained in the optical film of the present invention is dissolved. The shift to a longer wavelength is a shift occurring when the compound (1) is dispersed among molecular chains formed by the polymerized polymerizable liquid crystal compound, and the shift indicates that the compound (1) strongly interacts with the molecular chains. The shift to a longer wavelength means that an absorption maximum difference ($\lambda_{max1}-\lambda_{max2}$) is a positive value, and the difference is preferably 10 nm or more, more preferably 30 nm or more.

The dichroic ratio shown by the optical film of the present invention is 30 or more, preferably 40 or more, more preferably 50 or more.

When the base material used is not a quarter-wave plate, a circular polarizing plate can be obtained by laminating the resulting optical film (polarizing film) of the present invention and the quarter-wave plate. Here, it is preferred to perform the lamination in such a manner that the transmission axis of the optical film of the present invention and the slow axis (optical axis) of the quarter-wave plate form an angle of substantially 45°. A circular polarizing plate serving as an optical compensation film can also be obtained by making the transmission axis of the optical film (polarizing film) of the present invention coincident with or orthogonal to the optical axis of a phase difference film such as a quarter-wave plate.

The lamination of the optical film of the present invention and the quarter-wave plate may be performed together with a base material provided with the optical film of the present invention, or a base material provided with an orientation film, or may be performed after removal of the base material, or the base material and the orientation film. The base material, or the optical film of the present invention which is formed on a surface of the base material which is provided with the orientation film can be laminated with the quarter-wave plate by, for example, bonding the surface provided with the polarizing film of the present invention and the quarter-wave plate to each other by use of an adhesive, followed by removing the base material, or the base material provided with the optical film. Here, the adhesive may be applied to the optical film of the present invention, or applied to the quarter-wave plate.

<Uses of Optical Film>

The optical film (polarizing film) and the circular polarizing plate can be used in various display devices.

The display device is a device including a display element. The display device includes a light emitting element or a light emitting device as a light emitting source. Examples of the display device include liquid crystal display devices, organic electroluminescence (EL) display devices, inorganic electroluminescence (EL) display devices, touch panel display devices, electron emission display devices (field emission display devices (FED etc.) and surface field emission devices (SED)), electronic papers (display devices using electronic inks and electrophoretic elements), plasma display devices, projection-type display devices (grating light valve (GLV) display devices, display devices including digital micromirror devices (DMD) and so on) and piezoelectric ceramic displays. The liquid crystal display devices include all of transmission-type liquid crystal display devices, semi-transmission-type liquid crystal display devices, reflection-type liquid crystal display devices, direct view-type liquid crystal display devices, projection-type liquid crystal display devices and so on. These display devices may be display devices which display two-dimensional images, or stereoscopic display devices which display three-dimensional images. Particularly, the circular polarizing plate can be effectively used in organic EL display devices and inorganic EL display devices, and the optical compensation polarizing plate can be effectively used in liquid crystal display devices and touch panel display devices.

Embodiment 3: Compound (1); Embodiment 4: Method for Producing Compound (1); and Embodiment 5: Method for Producing Compound (3)

A compound according to embodiment 3 of the present invention is a compound represented by the following general formula (1), i.e. the above-mentioned compound (1). Groups in the compound (1) are the same as the above-mentioned groups.

[Chemical Formula 25]

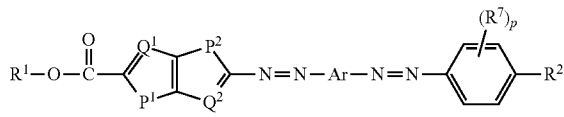

(1)

[in the general formula (1), $R^1$ represents an alkyl group having 1 to 11 carbon atoms;
$P^1$ and $P^2$ each independently represent —S—, —O— or —N($R^{12}$)—, $R^{12}$ represents a hydrogen atom or an alkyl group having 1 to 4 carbon atoms, and $Q^1$ and $Q^2$ each independently represent =N— or =CH—;
Ar represents a group represented by the following general formula (Ar-1) or (Ar-2):

[Chemical Formula 26]

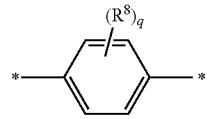

(Ar-1)

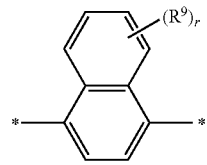

(Ar-2)

(in the above general formula, * represents a binding part with N);
$R^2$ represents a group selected from the following groups:

[Chemical Formula 27]

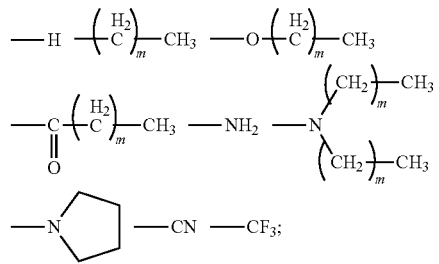

$R^7$ to $R^9$ are substituents other than a hydrogen atom, and each independently represent an alkyl group having 1 to 4 carbon atoms, an alkoxy group having 1 to 4 carbon atoms, a halogen atom or a cyano group, and one or more of hydrogen atoms in the alkyl group or the alkoxy group may be substituted with a halogen atom or a hydroxy group; m represents an integer of 0 to 10, and when one group has two occurrences of m, the two occurrences of m may be mutually the same or different; and p, q and r each independently represent an integer of 0 to 2].

A method for producing a compound (compound (1)) represented by the following general formula (1) according to embodiment 4 of the present invention includes a step of reacting a compound represented by the following general formula (3), (5) or (6) (also referred to as a compound (3), (5) or (6), respectively) and a compound represented by the following general formula ($R^1$-2) (hereinafter, also referred to as a compound ($R^1$-2)).

[Chemical Formula 28]

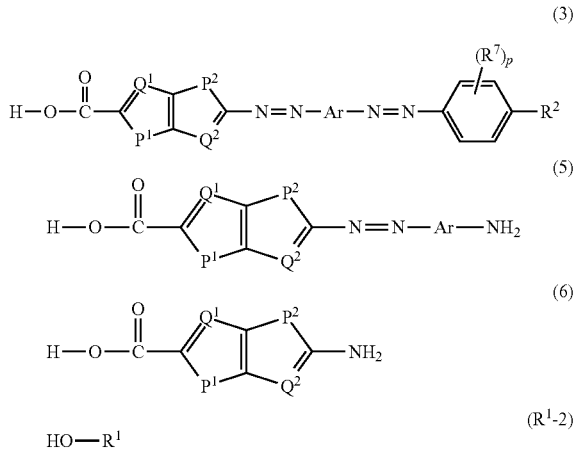

[in the above general formula, $R^1$, $R^2$, $R^{12}$, $R^7$ to $R^9$, $P^1$, $P^2$, $Q^1$, $Q^2$ and Ar are the same as shown in the general formula (1); and m, p, q and r are integers in the same range as shown in the general formula (1)].

A method for producing a compound (compound (3)) represented by the general formula (3) according to embodiment 5 of the present invention includes reacting a compound represented by the following general formula (5-1) and a compound represented by the following general formula ($R^2$-1) in the presence of N-methylpyrrolidone, N,N-dimethylformamide, N,N-dimethylacetamide or dimethylsulfoxide.

[Chemical Formula 29]

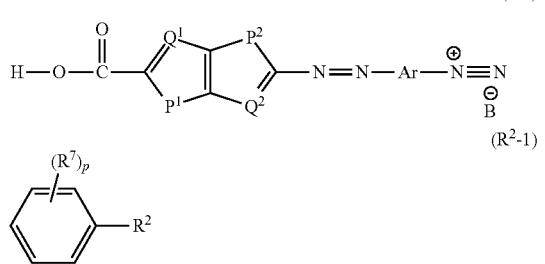

-continued

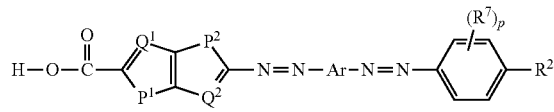

[in the above general formula, to $R^9$, $R^2$, $R^{12}$, $R^7$ to $P^1$, $P^2$, $Q^1$, $Q^2$ and Ar are the same as shown in the general formula (1); and m, p, q and r are integers in the same range as shown in the general formula (1); and B represents an anion].

$B^-$ usually represents an anion of a proton acid represented by HB, and examples of the anion represented by $B^-$ include a chloride ion, a hydrogen sulfate ion and a dihydrogen phosphate ion.

For obtaining at least two compounds (1) having mutually different structures in the method for producing the compound (1) according to the present invention, the method preferably includes a step of reacting a compound (compound (3), (5) or (6)) represented by the general formula (3), (5) or (6) and at least two compounds (compounds ($R^1$-2)) which have mutually different structures and which are represented by the general formula ($R^1$-2). When at least two compounds ($R^1$-2) having mutually different structures are reacted with the compound (3), (5) or (6), at least two compounds (1) having mutually different structures can be obtained in one reaction. When the composition of the present invention contains at least two compounds (1) having mutually different structures as described above, the stability of the composition can be improved, and as a result, productivity of the optical film of the present invention can be improved. In other words, by using at least two compounds ($R^1$-2) having mutually different structures, at least two compounds (1) which have mutually different structures and which are more suitable for production of the optical film can be easily produced.

Preferably, the method for producing the compound (1) according to the present invention includes a step of reacting the compound (3) and the compound ($R^1$-2) to obtain the compound (1) at the end as in a specific method as described later. In the above-mentioned step, the carbonyl group at the end of the compound (3) is esterified to produce the compound (1). Here, by using at least two compounds ($R^1$-2) having mutually different structures, at least two compounds (1) having the same structure except for being different in $R^1$ can be easily produced.

Hereinafter, one example of a production method according to the present invention will be described on the basis of schemes which specifically show a method for producing a compound (1-3) being one of the compounds (1). In the schemes 1 to 3 shown below, a specific compound included in a compound (X) (X=1, 3, 5, 6, 5-1, $R^1$-2 or $R^1$-1) is referred to as a compound (X-1A).

Scheme 1

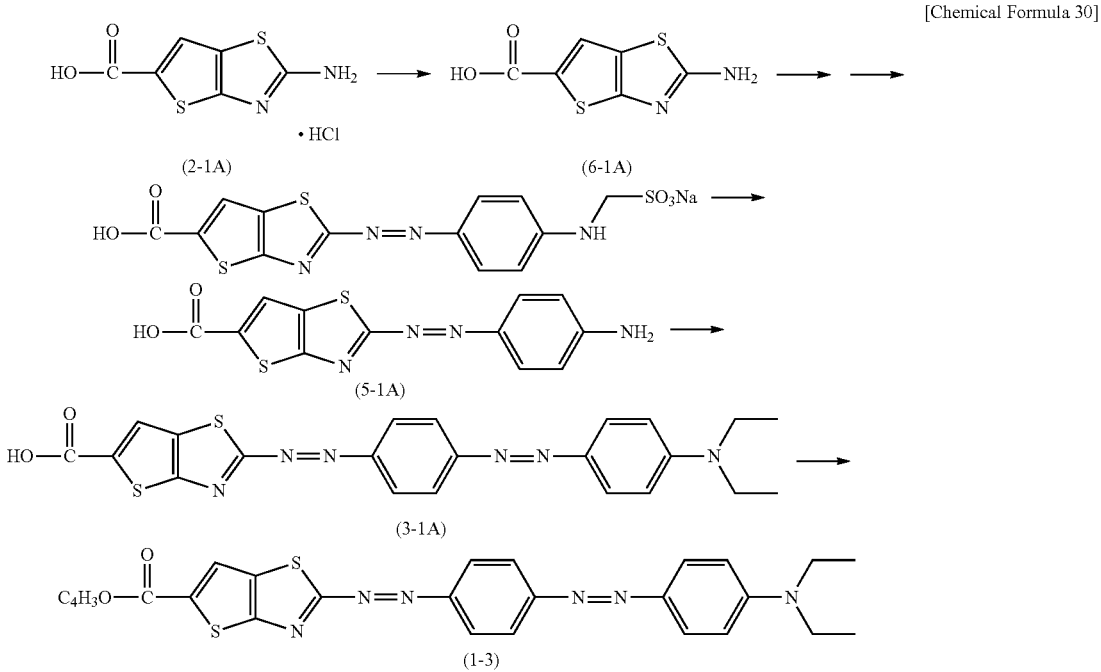

[Chemical Formula 30]

As shown in the scheme 1, a compound represented by the general formula (2-1A) (hereinafter, referred to as a compound (2-1A) can be used as a starting material. As the compound (2-1A), for example, a commercial product such as one manufactured by UORSY Building Blocks Library Company can be used.

First, the (2-1A) is treated with a base to prepare a compound (6-1A). The base is not particularly limited, and sodium hydroxide, potassium hydroxide or the like can be used. As the base, one base, or a mixture of two or more bases may be used.

Subsequently, a compound (5-1A) is prepared from the compound (6-1A). As a method for preparing the compound (5-1), a method conforming to the method described in JP-A-2009-215442 can be used.

Further, a compound (3-1A) is synthesized from the compound (5-1A) in accordance with the scheme 2 shown below. Detailed reaction conditions etc. for the synthesis will be shown below.

Scheme 2

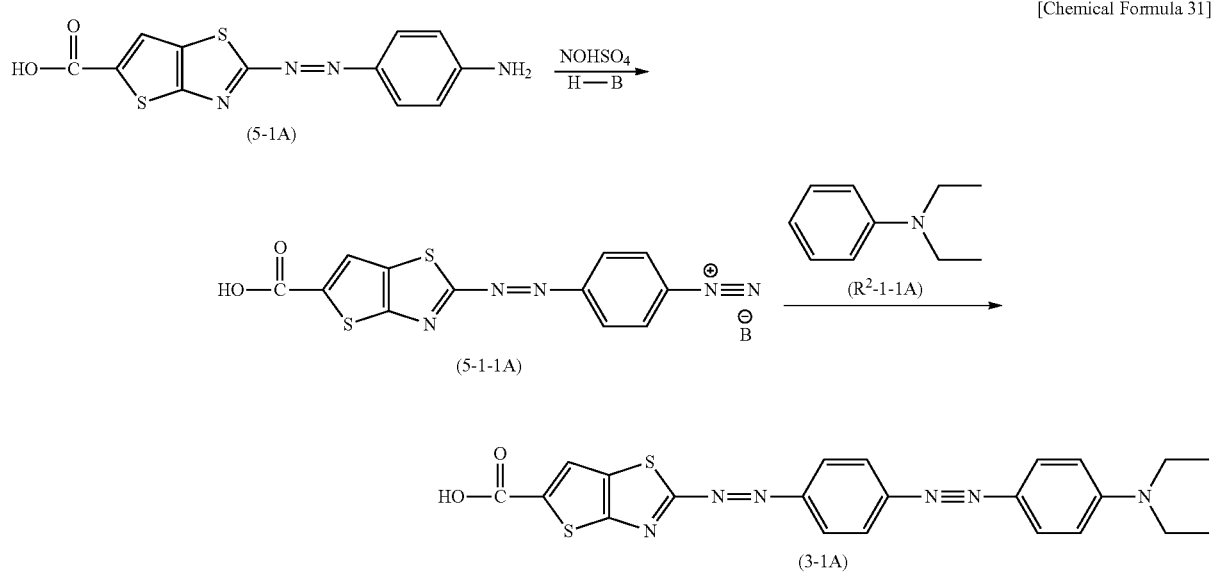

[Chemical Formula 31]

First, a compound (5-1-1A) is prepared by diazotizing the compound (5-1A) using a diazotization agent such as sodium nitrite or nitrosylsulfuric acid in the presence of a proton acid such as sulfuric acid, phosphoric acid or hydrochloric acid. As the proton acid, one proton acid, or a mixture of two or more proton acids may be used. As the diazotization agent, one diazotization agent, or a mixture of two or more diazotization agents may be used. The reaction may be carried out in the presence or absence of a solvent. The proton acid may be utilized as a part of the solvent by using an excessive amount of the proton acid. The reaction temperature here can be set in an appropriate range according to the kind of the compound (5-1A) to be used, and is, for example, in the range of −20 to 100° C. The reaction time can be set in the following manner: a reaction mixture during reaction is analyzed by liquid chromatography or gas chromatography to quantitatively determine and confirm the degree of consumption of the compound (5-1A) and/or the degree of generation of the compound (5-1-1A). Potassium nitrite and/or nitrosylsulfuric acid can be used in place of sodium nitrite. After completion of the reaction, the resulting compound (5-1) is usually used in a next reaction in the form of a mixture, but may be isolated or purified.

Next, the resulting compound (5-1-1A) is subjected to a diazo coupling reaction with a compound (R²-1-1A) to prepare a compound (3-1A). Here, when an aromatic compound other than the compound (R²-1-1A) is reacted, a bis-azo compound having a different substituent can be synthesized. The reaction temperature here can be set in an appropriate range according to the kind of the compound (5-1-1A), and is, for example, in the range of −20 to 100° C. The reaction solvent can be appropriately selected according to the kind of the compound (5-1-1A), and for example, at least one solvent selected from the group consisting of water, methanol, ethanol, 1-propanol, 2-propanol, N-methylpyrrolidone, N,N-dimethylformamide, N,N-dimethylacetamide and dimethylsulfoxide, preferably N-methylpyrrolidone, N,N-dimethylformamide, N,N-dimethylacetamide and dimethylsulfoxide can be used. The reaction time can be set in the following manner: a reaction mixture during reaction is analyzed by liquid chromatography or gas chromatography to quantitatively determine and confirm the degree of consumption of the compound (5-1-1A) and/or the degree of generation of the compound (3-1A).

When the mixture containing the compound (3-1A) after completion of the reaction is filtered and washed with an appropriate solvent, a solid of the compound (3-1A) can be obtained. As a washing solvent, a compound identical to the reaction solvent is usually used, but a compound different from the reaction solvent may be used. The resulting solid is used in a next reaction after being dried under reduced pressure, but may be purified by one of the methods: silica gel column chromatography, repulping, recrystallization and reprecipitation, or a combination of two or more thereof.

Finally, a compound (1-3) is synthesized from the compound (3-1A) in accordance with the scheme 3 shown below. Detailed reaction conditions etc. for the synthesis will be shown below.

Scheme 3

[Chemical Formula 32]

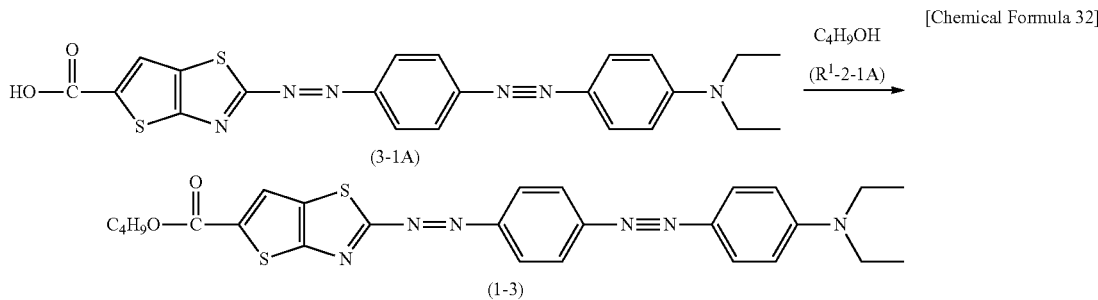

First, a compound (R¹-2-1A) is added to the compound (3-1A). The added amount of the compound (R¹-2-1A) may be appropriately changed according to the solubility of the compound (3-1A), and for example, the mass ratio of the compound (R¹-2-1A) to the compound (3-1A) is in the range of 1 to 500. Toluene or benzene may be added as a solvent. Subsequently, sulfuric acid is added, and the mixture is heated and stirred. The added amount of the sulfuric acid may be appropriately changed, and for example, the molar ratio of the sulfuric acid to the compound (3-1A) is 0.01 to 10. The reaction temperature here can be set in an appropriate range according to the kind of the compound (3-1A) and/or compound (R'-2-1A) to be used, and is, for example, in the range of 20 to 150° C. The reaction time can be set in the following manner: a reaction mixture during reaction is analyzed by liquid chromatography or gas chromatography to quantitatively determine and confirm the degree of consumption of the compound (3-1A) and/or the degree of generation of the compound (1-3).

The sulfuric acid can be replaced by various kinds of dehydration condensation reagents. The sulfuric acid can be replaced by, for example, an IPC (N,N-diisoorpylcarbodiimide)/DMAP (N,N-dimethylaminopyridine) mixture-based dehydration condensation reagent.

When the mixture containing the compound (1-3) after completion of the reaction is subjected to washing with water by liquid separation operation and concentration and dryness of an organic layer, or crystallization using a poor solvent, a solid of the compound (1-3) can be obtained.

Various kinds of solvents can be used in the organic layer in liquid separation operation, and for example, an ester solvent such as ethyl acetate can be used. As the poor solvent in crystallization, for example, hexane or heptane can be used. Preferably, the LC purity (area %/254 nm) of the resulting solid is set to 90% or more by repeating purification using one of the methods: silica gel column chromatography, resulting, recrystallization and reprecipitation, or a combination of two or more thereof.

Various compounds (1) can be obtained by appropriately changing the starting material, the compound (3), the compound (5), the compound (6), the compound (R$^1$-2), the compound (R$^2$-1) and other chemicals to be used according to an intended compound (1) while conforming to the above-mentioned method.

The present invention is not limited to the embodiments described above, and various changes can be made within the scope shown in claims. The technical scope of the present invention also includes embodiments obtained by appropriately combining technical means disclosed in different embodiments. Further, new technical features can be developed by combining technical means disclosed in the embodiments.

EXAMPLES

Hereinafter, the present invention will be described further in detail by way of examples, but the present invention should not be limited to these examples. The terms "%" and "parts" described in examples refer to "% by mass" and "parts by mass", respectively, unless otherwise specified.

[Preparation of Dichroic Dye]

A dichroic dye to be used in examples was prepared using method described in Production Example 1 below.

Production Example 1

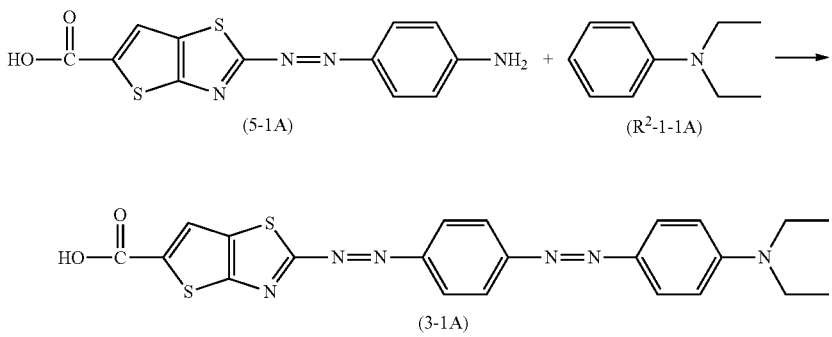

[Chemical Formula 33]

0.50 g of a compound (5-1A) and 17.5 g of 85% phosphoric acid were stirred and mixed at 80° C. for 5 minutes to obtain a mixture (a). The resulting mixture (a) was cooled to 0° C., 4.7 g of 40% nitrosylsulfuric acid was then added dropwise, and the mixture was stirred for 30 minutes to obtain a mixture (b). The resulting mixture (b) was added dropwise into a mixture (c) containing 2.9 g of N,N-diethylaniline as a compound (R$^2$-1-1A), 6.7 g of sodium acetate, 58.8 g of N-methylpyrrolidone, 44.1 g of methanol and 14.7 g of water at 0° C., and the mixture was stirred, heated to room temperature, and then stirred for 1 hour to obtain a mixture (d). A precipitate precipitated from the mixture (d) and containing a compound (3-1A) was filtered to obtain a solid. The resulting solid was washed with a mixed solvent of water and methanol (1:1), and then dried under reduced pressure to obtain 0.51 g of a compound (3-A). Properties etc. of the resulting compound (3-A) are shown below.
Yield: 67% (in terms of compound (5-1A))
Mw: 464 (LC-MS)
Maximum absorption wavelength ($\lambda_{max2}$)=554 nm (tetrahydrofuran solution)

Subsequently, a compound (1-3) was prepared using the resulting compound (3-A).

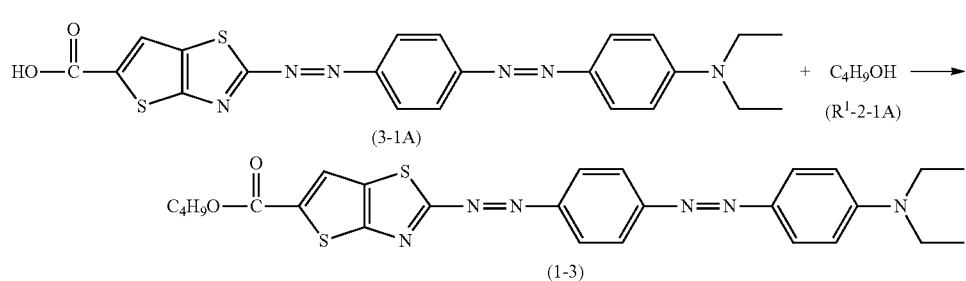

[Chemical Formula 34]

0.13 g of a compound (3-1A), 15.0 g of 1-butanol as a compound (R'-2-1A) and 0.025 g of 98% sulfuric acid were mixed at room temperature for 5 minutes, the mixture was then heated to 100° C., and stirred for 4 hours to obtain a mixture (e). The resulting mixture (e) was returned to room temperature, 10 g of ethyl acetate and 10 g of water were added, and the mixture was mixed to obtain a mixture (f). An organic layer of the resulting mixture (f) was separated, and the organic layer was washed with water, and then dried under reduced pressure to obtain a solid.

The resulting solid was purified by silica gel column chromatography (eluent: chloroform/heptane=5/1 to 20/1). The resulting solid was washed with a mixed solvent of water and methanol (1:2), and then dried to obtain 0.04 g of a compound (1-3) as a blue solid.

Properties etc. of the resulting compound (1-3) are shown below.

Yield: 24% (in terms of compound 3-1A)
Mw: 520 (LC-MS)
Maximum absorption wavelength ($\lambda_{max2}$)=572 nm (chloroform solution).

[Preparation of Polymerizable Liquid Crystal Compound]

A polymerizable liquid crystal compound to be used in examples was prepared using the method described in Production Example 2 below.

Production Example 2

A polymerizable liquid crystal compound: a compound represented by the following chemical formula (4-6) (hereinafter, referred to as a compound (4-6)) was prepared using a method as described in the prior art document: Lub et al. Recl. Trav. Chim. Pays-Bas, 115, 321-328 (1996). Further, a polymerizable liquid crystal compound: a compound represented by the following chemical formula (4-8) (hereinafter, referred to as a compound (4-8)) was prepared using a method conforming to the method the above-mentioned prior art document.

[Chemical Formula 35]

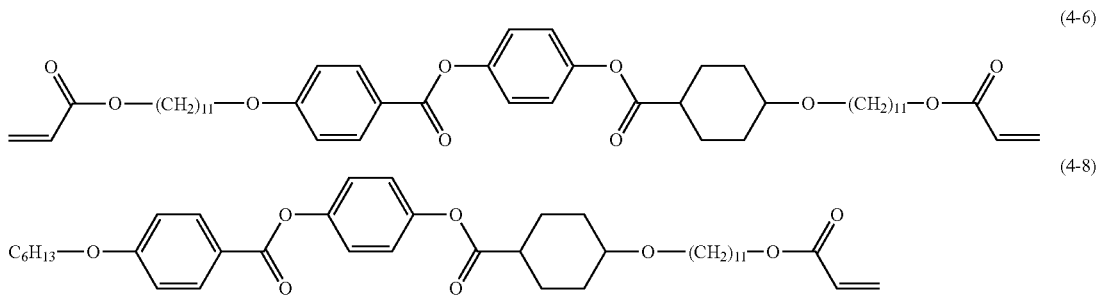

[Measurement of Phase Transition Temperature]

The phase transition temperatures of the compound (4-6) and the compound (4-8) were measured using the method shown below.

A film composed of the compound (4-6) or the compound (4-8) was formed on a glass substrate provided with an orientation film, and the phase transition temperature was measured by performing texture observation with a polarizing microscope (BX-51 manufactured by Olympus Corporation) while applying heat.

As a result, the compound (4-6) underwent phase transition to a nematic phase at 112° C., phase transition to a smectic A phase at 110° C., and phase transition to a smectic B phase at 94° C. during temperature falling after the temperature was raised to 120° C. The compound (4-8) underwent phase transition to a nematic phase at 131° C., phase transition to a smectic A phase at 80° C., and phase transition to a smectic B phase at 68° C. during temperature falling after the temperature was raised to 140° C.

Example 1

[Preparation of Composition]

The compounds and chemicals shown below were mixed, and the mixture was stirred at 80° C. for 1 hour to obtain a composition (1).

Polymerizable Liquid Crystal Compound:
compound (4-6) (75 parts)
compound (4-8) (25 parts)
Compound (1): compound (1-3) (2.9 parts)
Polymerization Initiator:
2-dimethylamino-2-benzyl-1-(4-morphorinophenyl)butane-1-one (IRGACURE 369; manufactured by Ciba Specialty Chemicals Inc.) (6 parts)

Leveling agent: polyacrylate compound (BYK-361N manufactured by BYK-Chemie GmbH) (1.5 parts)

Solvent: mixed solvent of xylene and isophorone (95:5) (250 parts).

[Preparation and Evaluation of Optical Film]

Using the methods shown below, a polarizing film (1) as an optical film was prepared, and the physical properties etc. thereof were evaluated.

<1. Formation of Orientation Film>

A 2 mass % aqueous solution of polyvinyl alcohol (Polyvinyl Alcohol 1000 (fully saponified) manufactured by Wako Pure Chemical Industries, Ltd.) was applied onto a glass substrate by a spin coating method, and dried to form a 100 nm-thick film. Subsequently, a surface of the resulting film was subjected to a rubbing treatment to form an orientation film. The rubbing treatment was performed with a cloth (trade name: YA-20-RW, manufactured by YOSHIKAWA CHEMICAL CO., LTD.) under the conditions of a pushing depth of 0.15 mm, a rotation number of 500 rpm and a rate of 16.7 mm/s using a semiautomatic rubbing apparatus (trade name: Model LQ-008, manufactured by JOYO ENGINEERING CO., LTD.). A laminate 1 with an orientation film formed on a glass substrate was obtained through the rubbing treatment.

<2. Formation of Polarizing Film>

The composition (1) was applied onto the orientation film of the laminate 1 by a spin coating method, heated and dried on a hot plate at 120° C. for 1 minute, and then quickly cooled to room temperature to form a dry film containing a polymerizable liquid crystal compound oriented on the orientation film. The dry film was then irradiated with an ultraviolet ray in an exposure amount of 1500 mJ/cm$^2$ (365 nm basis) using an UV irradiation apparatus (SPOT CURE SP-7 manufactured by USHIO INC.), whereby the polymerizable liquid crystal compound contained in the dry film was polymerized while the oriented state was retained, so that a polarizing film (1) was formed from the dry film to obtain a laminate 2. The thickness of the polarizing film (1) was measured with a laser microscope (OLS 3000 manufactured by Olympus Corporation), and the result showed that the thickness of the polarizing film (1) was 1.7 µm.

<3. Measurement of Dichroic Ratio>

An absorbance ($A^1$) in a transmission axis direction and an absorbance ($A^2$) in an absorption axis direction at a maximum absorption wavelength were measured by a double beam method using an apparatus in which a folder provided with the laminate 2 was set in a spectrophotometer (UV-3150 manufactured by Shimadzu Corporation). A mesh for cutting a light amount by 50% was installed on the reference side of the folder. From the measured values of the absorbance ($A^1$) in the transmission axis direction and the absorbance ($A^2$) in the absorption axis direction, the ratio ($A^2/A^1$) of the absorbances was calculated, and defined as a dichroic ratio.

Maximum absorption wavelength ($\lambda_{max}$): 656 nm

Dichroic ratio (maximum absorption wavelength): 45.

<4. Evaluation of Light Resistance>

A protective film (40 µm TAC ("KC 4UY" manufactured by Konica Minolta Opto Co., Ltd.) was disposed on a surface of the formed polarizing film (1), and irradiated with light under the following conditions to evaluate light resistance. The absorbance of the polarizing film (1) at a maximum absorption wavelength of 656 nm after the light resistance test was 95% of that before the test. Using a dichroic dye as described in JP-A-2013-101328 (Example 4), a polarizing film was formed by the same method as described above, and a light resistance test was conducted. As a result, it was shown that the absorbance of the polarizing film at a maximum absorption wavelength of 610 nm after the light resistance test was 87 of that before the test. The results are shown in Table 1.

Light irradiation conditions in the light resistance test are as follows.

Device used: SUNTEST XLS+ manufactured by ATLAS Company

Light source used: xenon arc lamp

Exposure condition: 250 mW/m$^2$

Test time: 120 hours

Exposure amount: 108000 KJ/m$^2$

Temperature: 60° C.

TABLE 1

| | Molecular structure | λ max | Dichroic ratio | Light resistance * |
|---|---|---|---|---|
| Example 3 | C$_4$H$_9$—O—C(=O)—[thienothiazole]—N=N—[phenyl]—N=N—[phenyl]—N(ethyl)$_2$ | 656 nm | 45 | 95% |
| Comparative Example 1 | C$_4$H$_9$—[thienothiazole]—N=N—[phenyl]—N=N—[phenyl]—N(ethyl)$_2$ | 610 nm | 34 | 87% |

* Light resistance = (absorbance at maximum absorption wavelength after light resistance test)/(absorbance at maximum absorption wavelength before light resistance test)

Conclusions

From the results of measurement of the dichroic ratio, it was found that the maximum absorption wavelength ($\lambda_{max2}$) of the compound (1-3) in chloroform was 572 nm, and therefore a shift to a longer wavelength occurred. The occurrence of a shift to a longer wavelength showed that when the compound (1-3) was dispersed among dense molecular chains formed by polymerization of the polymerizable liquid crystal compound in the optical film of the present invention, the compound (1-3) strongly interacted with the molecular chains. Thus, it was apparent that the optical film of the present invention had a maximum absorption at a wavelength in the range of 600 to 680 nm and had a high dichroic ratio.

The optical film of the present invention was superior in light resistance as is apparent from the evaluation of light resistance, particularly from the descriptions in Table 1.

An optical film formed from the composition of the present invention, or the optical film of the present invention is superior in light resistance to conventional optical films. Therefore, the optical film (polarizing film) of the present invention can be widely used in the field of production of liquid crystal display devices, liquid crystal cells, circular polarizing plates and organic EL display devices, each of which includes such an optical film.

What is claimed is:

1. An optical film comprising: a polymer of a polymerizable liquid crystal compound; and a compound represented by the following general formula (1):

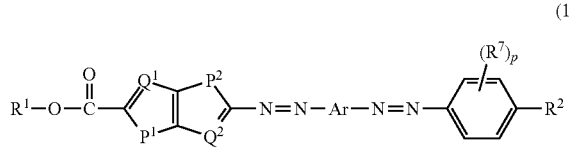

wherein:
$R^1$ represents an alkyl group having 1 to 11 carbon atoms;
$P^1$ and $P^2$ each independently represent —S—, —O— or —N($R^{12}$)—, $R^{12}$ represents a hydrogen atom or an alkyl group having 1 to 4 carbon atoms, and $Q^1$ and $Q^2$ each independently represent =N— or =CH—;
Ar represents a group represented by the following general formula (Ar-1) or (Ar-2):

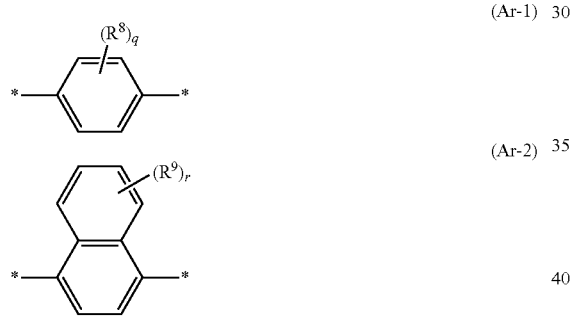

wherein * represents a binding part with N;
$R^2$ represents a group selected from the following groups:

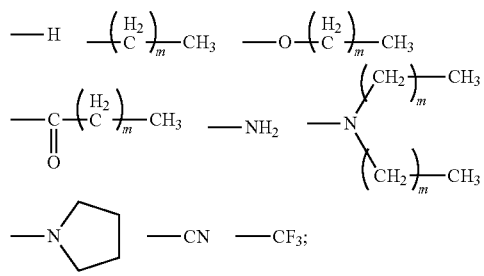

$R^7$ to $R^9$ are substituents other than a hydrogen atom, and each independently represent an alkyl group having 1 to 4 carbon atoms, an alkoxy group having 1 to 4 carbon atoms, a halogen atom or a cyano group, and one or more of hydrogen atoms in the alkyl group or the alkoxy group may be substituted with a halogen atom or a hydroxy group;
m represents an integer of 0 to 10, and when one group has two occurrences of m, the two occurrences of m may be mutually the same or different; and p, q and r each independently represent an integer of 0 to 2.

2. The optical film according to claim 1, wherein the compound represented by the general formula (1) is a compound represented by the following general formula (2):

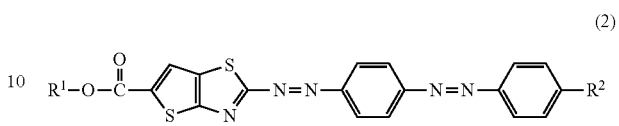

wherein $R^1$ and $R^2$ have the same meaning as $R^1$ and $R^2$ in the general formula (1).

3. The optical film according to claim 1, comprising two or more compounds which have mutually different structures and which are represented by the general formula (1).

4. The optical film according to claim 3, wherein the two or more compounds which have mutually different structures and which are represented by the general formula (1) have mutually different structures only in $R^1$ in the general formula (1).

5. The optical film according to claim 1, wherein the polymerizable liquid crystal compound is a compound which shows a smectic liquid crystal phase.

6. The optical film according to claim 1, wherein the polymerizable liquid crystal compound is a compound represented by the following general formula (4):

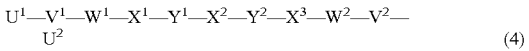

wherein $X^1$, $X^2$ and $X^3$ each independently represent a 1,4-phenylene group optionally having a substituent, or a cyclohexane-1,4-diyl group optionally having a substituent, with the proviso that at least one of $X^1$, $X^2$ and $X^3$ is a 1,4-phenylene group optionally having a substituent, and —$CH_2$— in the cyclohexane-1,4-diyl group may be substituted with —O—, —S— or —NR—, where R represents an alkyl group having 1 to 6 carbon atoms, or a phenyl group;
$Y^1$ and $Y^2$ each independently represent a single bond, —$CH_2CH_2$—, —$CH_2O$—, —COO—, —OCOO—, —N=N—, —$CR^a$=$CR^b$—, —C≡C— or —$CR^a$=N—, where $R^a$ and $R^b$ each independently represent a hydrogen atom or an alkyl group having 1 to 4 carbon atoms;
$U^1$ represents a hydrogen atom or a polymerizable group;
$U^2$ represents a polymerizable group;
$W^1$ and $W^2$ each independently represent a single bond, —O—, —S—, —COO— or —OCOO—; and
$V^1$ and $V^2$ each independently represent an alkanediyl group having 1 to 20 carbon atoms and optionally having a substituent, and —$CH_2$— in the alkanediyl group may be substituted with —O—, —S— or —NH—.

7. A composition including a polymerizable liquid crystal compound, and a compound represented by the following general formula (1):

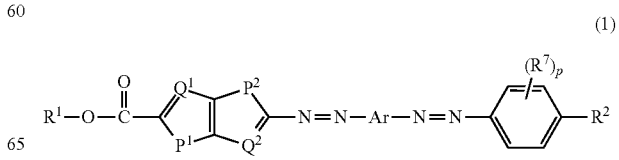

wherein:

$R^1$ represents an alkyl group having 1 to 11 carbon atoms;
$P^1$ and $P^2$ each independently represent —S—, —O— or —N($R^{12}$)—, $R^{12}$ represents a hydrogen atom or an alkyl group having 1 to 4 carbon atoms, and $Q^1$ and $Q^2$ each independently represent =N— or =CH—;

Ar represents a group represented by the following general formula (Ar-1) or (Ar-2):

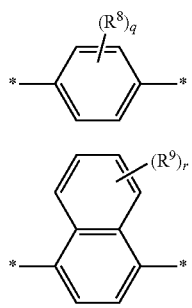

wherein * represents a binding part with N;
$R^2$ represents a group selected from the following groups:

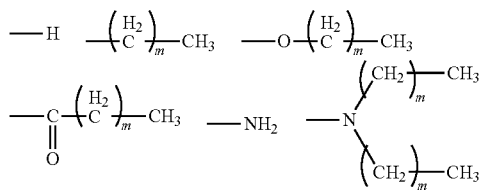

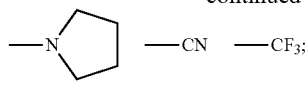

$R^7$ to $R^9$ are substituents other than a hydrogen atom, and each independently represent an alkyl group having 1 to 4 carbon atoms, an alkoxy group having 1 to 4 carbon atoms, a halogen atom or a cyano group, and one or more of hydrogen atoms in the alkyl group or the alkoxy group may be substituted with a halogen atom or a hydroxy group;

m represents an integer of 0 to 10, and when one group has two occurrences of m, the two occurrences of m may be mutually the same or different; and p, q and r each independently represent an integer of 0 to 2.

8. The composition according to claim 7, comprising two or more compounds which have mutually different structures and which are represented by the general formula (1).

9. An optical film which is formed of the composition according to claim 7.

10. A circular polarizing plate comprising the optical film according to claim 1.

11. A circular polarizing plate comprising the optical film according to claim 9.

12. A display device comprising the optical film according to claim 1.

13. A display device comprising the optical film according to claim 9.

* * * * *